United States Patent
Liu et al.

(10) Patent No.: US 9,266,982 B2
(45) Date of Patent: Feb. 23, 2016

(54) N ORTHO ACYL SUBSTITUTED NITROGEN-CONTAINING HETEROCYCLIC COMPOUND AND PROCESS FOR PREPARING AMINAL IRON (II) COMPLEXES THEREOF

(75) Inventors: Jun Liu, Beijing (CN); Mingfang Zheng, Beijing (CN); Weizhen Li, Beijing (CN); Haiying Zhang, Beijing (CN); Huaijie Wang, Beijing (CN); Yu Zhou, Beijing (CN); Tonglin Li, Beijing (CN); Lan Zhao, Beijing (CN); Hongfei Wu, Beijing (CN); Mingjun Xie, Beijing (CN); Chunhong Wu, Beijing (CN); Zhiguang Jia, Beijing (CN); Yanping Qi, Beijing (CN); Jilong Wang, Beijing (CN)

(73) Assignees: China Petroleum & Chemical Corporation, Beijing (CN); Beijing Research Institute of Chemical Industry, China Petroleum & Chemical Corporatin, Beijing (CN)

( * ) Notice: Subject to any disclaimer, the term of this patent is extended or adjusted under 35 U.S.C. 154(b) by 0 days.

(21) Appl. No.: 13/991,044

(22) PCT Filed: Dec. 1, 2011

(86) PCT No.: PCT/CN2011/002014
§ 371 (c)(1),
(2), (4) Date: May 31, 2013

(87) PCT Pub. No.: WO2012/071791
PCT Pub. Date: Jun. 7, 2012

(65) Prior Publication Data
US 2013/0267708 A1 Oct. 10, 2013

(30) Foreign Application Priority Data

| Dec. 1, 2010 | (CN) | 2010 1 0576813 |
| Dec. 1, 2010 | (CN) | 2010 1 0576856 |
| Dec. 1, 2010 | (CN) | 2010 1 0576860 |
| Dec. 1, 2010 | (CN) | 2010 1 0576875 |
| Dec. 1, 2010 | (CN) | 2010 1 0576892 |
| Sep. 1, 2011 | (CN) | 2011 1 0256330 |

(51) Int. Cl.
*C07D 471/04* (2006.01)
*C07D 211/70* (2006.01)
(Continued)

(52) U.S. Cl.
CPC .............. *C08F 110/02* (2013.01); *B01J 31/183* (2013.01); *C07C 2/32* (2013.01); *C07D 213/127* (2013.01); *C07D 471/04* (2013.01);
(Continued)

(58) Field of Classification Search
None
See application file for complete search history.

(56) References Cited

FOREIGN PATENT DOCUMENTS

| CN | 1389443 A | 1/2003 |
| CN | 1850339 A | 10/2006 |

(Continued)

OTHER PUBLICATIONS

Olah, GA. et al. Aromatic Substitution. XXXI. Acetylation of Benzene, Alkylbenzenes, and Halobenzenes with methyloxocarbonium (Acetylium) Hexafluoro- and Hexachloroantimonate. Journal of the American Chemical Society. 1964, vol. 86, p. 2203.*

(Continued)

*Primary Examiner* — Janet L Andres
*Assistant Examiner* — Ben S Michelson
(74) *Attorney, Agent, or Firm* — Finnegan, Henderson, Farabow, Garrett & Dunner, LLP

(57) ABSTRACT

Provided are a process for preparing an N ortho acyl substituted nitrogen-containing heterocyclic compound and an aminal iron (II) complex thereof, and the use of the complexes obtained by the process in an olefin oligomerization catalyst. The N ortho acyl substituted nitrogen-containing heterocyclic compound in the present invention is for example 2-acyl-1,10-phenanthroline or 2,6-diacetyl pyridine as shown in formula b, and the N ortho acyl substituted nitrogen-containing heterocyclic compound in the present invention is produced by a reaction of a precursor thereof in a substituted or unsubstituted nitrobenzene. Preferably the precursor shown in formula I in the present invention is produced by 1,10-phenanthroline reacting with trialkyl aluminum, or a halogenoalkyl aluminum $R_nAlX_m$, or a substituted or unsubstituted benzyl lithium Ph'CH$_2$Li, followed by hydrolysis. The preparation method provided in the present invention has a few synthetic steps, an easy process, a low toxic effect, and reduces the preparation costs of the catalyst, and has a promising outlook in the industrial application.

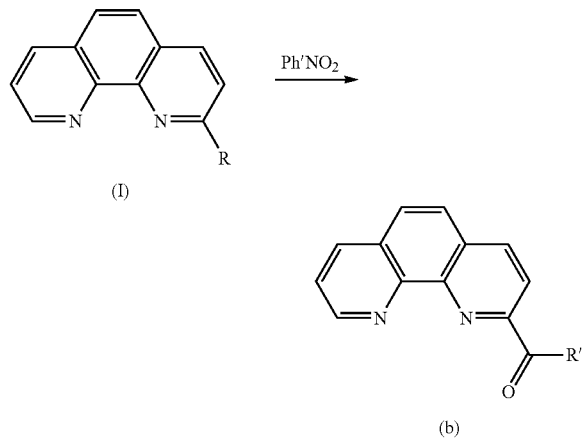

17 Claims, No Drawings

(51) Int. Cl.
| | |
|---|---|
| C07D 211/82 | (2006.01) |
| C07D 213/46 | (2006.01) |
| C08F 110/02 | (2006.01) |
| B01J 31/18 | (2006.01) |
| C07C 2/32 | (2006.01) |
| C07D 213/127 | (2006.01) |
| C07F 15/02 | (2006.01) |

(52) U.S. Cl.
CPC ............ *C07F 15/025* (2013.01); *B01J 2231/20* (2013.01); *B01J 2531/0241* (2013.01); *B01J 2531/842* (2013.01)

(56) References Cited

FOREIGN PATENT DOCUMENTS

| | | |
|---|---|---|
| CN | 101348501 A | 1/2009 |
| CN | 101823996 A * | 9/2010 |
| CN | 102485732 A | 6/2012 |
| CN | 102485733 A | 6/2012 |
| CN | 102485733 A | 6/2012 |
| CN | 102532201 A | 7/2012 |
| CN | 102556242 A | 7/2012 |
| CN | 102558241 A | 7/2012 |
| CN | 102964388 A | 3/2013 |
| EP | 0741682 B1 | 11/1996 |
| WO | WO 99/02472 A1 | 1/1999 |
| WO | WO 99/19275 A1 | 4/1999 |
| WO | WO 2008/152068 A2 | 12/2008 |

OTHER PUBLICATIONS

Lorente, A. et al. Syntheses and copper(II)-dependent DNA photocleavage by acridine and anthracene 1,10-phenanthroline conjugate systems. Org. Biomol. Chem. 2005, vol. 3, p. 1857.*

Olah, GA. et al. Aromatic Substitution. XXII. Acetylation of Benzene, Alkylbenzenes, and Halobenzenes with Methyloxocarbonium (Acetylium) Hexafluoro- and Hexachloroantimonate. J. Am. Chem. Soc. 1964, vol. 86, p. 2203.*

Johnstone, RA. et al. Heterogeneous Catalytic Transfer Hydrogenation and Its Relation to Other Methods for Reduction of Organic Compounds. Chem. Rev. 1985, vol. 85, p. 141.*

Dorwold, FZ. Side Reactions in Organic Synthesis. Wiley. 2005, preface.*

Sun, WH. et al. Iron Complexes Bearing 2-imino-1,10-phenanthrolinyl Ligands as Highly Active Catalysts for Ethylene Oligomerization. Organometallics. 2006, vol. 25, p. 667.*

Eicher, T. et al. The Chemistry of Heterocycles. 2008, p. 273.*

Britovsek et al., "Novel olefin polymerization catalysts based on iron and cobalt" *Chem. Commun.*, 849-850 (1998).

Britovsek et al., "Oligomerisation of ethylene by bis(imino)pyridyliron and -cobalt complexes" *Chem. Eur. J.*, 6(12):2221-2231 (2000).

Jie et al., "Iron(II) complexes ligated by 2-imino-1,10-phenanthrolines: Preparation and catalytic behavior toward ethylene oligomerization" *J. Mol. Catal. A: Chemical*, 269:85-96 (2007).

Xing et al., *Fundamental Organic Chemistry*, 3$^{rd}$ ed., High Educational Press, p. 917 (2005).

Li et al., *Heterocyclic Chemistry—Structure, Reaction, Synthesis and Application*, Chemical Industry Press, p. 273 (2008).

Small et al., "Iron-based catalysts with exceptionally high activities and selectivities for oligomerization of ethylene to linear α-olefins" *J. Am. Chem. Soc.*, 120:7143-7144 (1998).

Sun et al., "Iron complexes bearing 2-imino-1,10-phenanthrolinyl ligands as highly active catalysts for ethylene oligomerization" *Organometallics*, 25:666-677 (2006).

Zhang et al., "2-Ethyl-ketimino-1,10-phenanthroline iron(II) complexes as highly active catalysts for ethylene oligomerization" *J. Mol. Catal. A: Chemical*, 320: 92-96 (2010).

International Search Report mailed Mar. 22, 2012, issued in International Patent Application No. PCT/CN2011/002014.

Written Opinion mailed Mar. 22, 2012, issued in International Patent Application No. PCT/CN2011/002014.

* cited by examiner

N ORTHO ACYL SUBSTITUTED NITROGEN-CONTAINING HETEROCYCLIC COMPOUND AND PROCESS FOR PREPARING AMINAL IRON (II) COMPLEXES THEREOF

CROSS REFERENCE TO RELATED APPLICATIONS

This application is a national phase application based on PCT/CN2011/002014, filed Dec. 1, 2011, which claims the priority of Chinese Patent Application Nos. 201010576813.7, filed Dec. 1, 2010, 201010576856.5, filed Dec. 1, 2010, 201010576860.1, filed Dec. 1, 2010, 201010576875.8, filed Dec. 1, 2010, 201010576892.1, filed Dec. 1 2010, and 201110256330.3, filed Sep. 1, 2011, the contents of all of which are incorporated herein by reference.

TECHNICAL FIELD

The present invention relates to a process for preparing an olefin oligomerization catalyst, more specifically to a process for preparing an N ortho acyl substituted nitrogen-containing heterocyclic compound and an aminal iron (II) complex thereof, and a use of the complex obtained by the process in an olefin oligomerization catalyst.

TECHNICAL BACKGROUND

Ethylene oligomerization is one of the most important reactions in the industry of olefin polymerization. Low cost small molecular olefins can be converted into high value-added products by oligomerization. Ethylene oligomerization products, i.e., linear alpha olefins (LAO) are important organic chemical raw materials. For example, $C_4$-$C_{30}$ LAO can be used for preparing household cleaners, flotation agents, emulsifying agents, lubricant components for refrigerants or drilling fluids, plasticizers, various additives, low-viscosity synthetic oils, polymers, copolymers, additives for oil or oil products, higher alkyl amines, higher organoaluminum compounds, higher alkaryl hydrocarbons, higher fatty alcohols and fatty acids, epoxides, additives for heat carriers, and so on. Adhesives, sealants and paint can also be synthesized based on $C_{20}$-$C_{30}$ LAO. Recently, with the development of the polyolefin industry, the worldwide demands for alpha olefins grow rapidly, wherein, most alpha olefins are prepared based on ethylene oligomerization.

The catalysts used in ethylene oligomerization mainly include nickel-based, chromium-based, zirconium-based, and aluminum-based catalyst systems, and so on. Recently, the complexes of iron (II) or cobalt (II) with imino-pyridyl tridentate ligands for catalyzing ethylene oligomerization have been reported respectively by Brookhart's group (see Brookhart M et al, J. Am. Chem. Soc., 1998, 120, 7143-7144 and WO99/02472 published in 1999) and Gibson's group (see Gibson V. C. et al, Chem. Commun., 1998, 849-850 and Chem. Eur. J., 2000, 2221-2231), in which both the catalytic activity and selectivity of alpha olefins are high. Therefore, such complexes have a promising prospect in the industrial application. As to such complex catalysts of iron (II) or cobalt (II), the synthesis of ligands is the key point. Whether such complexes can be obtained and the cost thereof are determined by the synthesis method of ligands.

In the prior art, for example, in organic chemistry textbooks *Heterocyclic Chemistry—Structure, Reaction, Synthesis and Application* (Li Runtao, Ge Zemei, Wang Xin, translation, Chemical Industry Press, 2008, 1 (1): 273) and *Fundamental Organic Chemistry* (Xing Qiyi, et., Higher Education Press, 2005, 12 (3):917), it both discloses using nitrobenzene as an oxidant to oxide the hydrogen linked with N in nitrogen-containing heterocyclic compounds. However, it does not disclose that when nitrobenzene is used as an oxidant, an acyl at the ortho position of nitrogen can be generated.

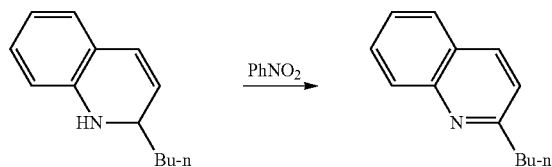

Sun Wenhua's group of Institute of Chemistry, Chinese Academy of Sciences (see Sun Wenhua et. al., Journal of *Organometallics* 25 (2006) 666-677) first adopts 1,10-phenanthroline imine compounds to coordinate with iron (II) so as to obtain tridentate nitrogen imine complexes, which are then used to catalyze ethylene oligomerization. Both the activity and selectivity of such catalyst are high. However, the defects of the preparing methods for such catalyst are that, the synthesis steps for ligands are too complicated, and that 2-acetyl-1,10-phenanthroline is obtained only when highly toxic potassium cyanide is involved in the reaction. In addition, CN101823996A discloses a process for preparing 2,8-diacyl quinoline, wherein selenium dioxide is substantially used in the oxidation reaction so as to generate 2-acyl quinoline. Such method can also be used to form 2-acyl-1,10-phenanthroline. But in the process, selenium dioxide itself is high toxic chemicals of high price and is difficult to be purchased.

Therefore, the development of a process for preparing ethylene oligomerization catalyst with less synthesis steps, simple processes, low raw material cost and free of high toxic substances has been attached great importance.

SUMMARY OF THE INVENTION

One object of the present invention is to provide a new process for preparing an ethylene oligomerization catalyst and the use of the prepared catalyst.

According to one aspect of the present invention, it provides a process for preparing an N ortho acyl substituted nitrogen-containing heterocyclic compound, wherein an N ortho hydroxyl substituted nitrogen-containing compound is obtained in a substituted or unsubstituted nitrobenzene Ph'$NO_2$ to generate the N ortho acyl substituted nitrogen-containing heterocyclic compound, the N ortho hydroxyl group comprises a methyl or methylene group which directly links with the nitrogen-containing heterocyclic compound, and the five substituent groups in the benzene ring of the substituted nitrobenzene can be hydrogen, a $C_1$-$C_6$ alkyl group, a $C_2$-$C_6$ alkenyl or alkynyl group, halogen, a $C_1$-$C_6$ alkoxy group or an nitro group independently.

The substituted phenyl group corresponding to said substituted nitrobenzene can be embodied as 2-methyl phenyl, 3-methyl phenyl, 4-methyl phenyl, 2,3-dimethyl phenyl, 2,4-dimethyl phenyl, 2,5-dimethyl phenyl, 2,6-dimethyl phenyl, 3,4-dimethyl phenyl, 3,5-dimethyl phenyl, 2,4,6-trimethyl phenyl, 4-bromo-2,6-dimethyl phenyl, 2-ethyl phenyl, 2-ethyl-6-methyl phenyl, 2-isopropyl phenyl, 2,6-diethyl phenyl, 2,6-diisopropyl phenyl, 2-fluoro phenyl, 2-fluoro-4-methyl phenyl, 2-fluoro-5-methyl phenyl, 2,4-difluoro phenyl, 2,5-difluoro phenyl, 2,6-difluoro phenyl, 3,4-difluoro phenyl, 2,3,4-trifluoro phenyl, 2,4,5-trifluoro phenyl, 2,4,6-trifluoro phenyl, 2,3,4,5,6-pentafluoro phenyl, 3-chloro phenyl, 2,6-chloro phenyl, 2,3,4-trichloro phenyl, 2,4,5-trichlorophenyl, 2,4,6-trichlorophenyl, 2-bromophenyl, 2-bromo-4-methyl phenyl, 2-bromo-4-fluorophenyl, 4-bromo-2-fluoro phenyl, 2,6-dibromo phenyl, 2,6-dibromo-4-methyl phenyl, 2,6-dibromo-4-chloro phenyl, 2,4,6-tribromo phenyl, 2-bromo-6-chloro-4-fluoro phenyl, 2-bromo-4-chloro-6-fluoro phenyl, 2-bromo-4,6-difluoro phenyl, 3-nitro phenyl, 4-methoxy phenyl, 2-methyl-4-methoxy phenyl, or 4-ethoxy phenyl.

In a preferable embodiment of the present invention, said N ortho acyl substituted nitrogen-containing heterocyclic compound is a substituted or unsubstituted 2-acyl pyridine as shown in formula B, a compound as shown in formula A reacts with a substituted or unsubstituted nitrobenzene to generate the compound as shown in formula B, wherein $R_1$ is selected from hydrogen, a $C_1$-$C_6$ alkyl group, a $C_2$-$C_6$ alkenyl or alkynyl group, a phenyl group and a substituted phenyl group, and $R_2$-$R_5$ can be hydrogen, a $C_1$-$C_6$ alkyl group, a $C_2$-$C_6$ alkenyl or alkynyl group, a halogen, a $C_1$-$C_6$ alkoxy group, a nitro group, a phenyl group or a substituted phenyl group independently; and the five substituent groups in the benzene ring of the substituted phenyl group can be a $C_1$-$C_6$ alkyl group, a $C_2$-$C_6$ alkenyl or alkynyl group, a halogen, a $C_1$-$C_6$ alkoxy group or a nitro group independently.

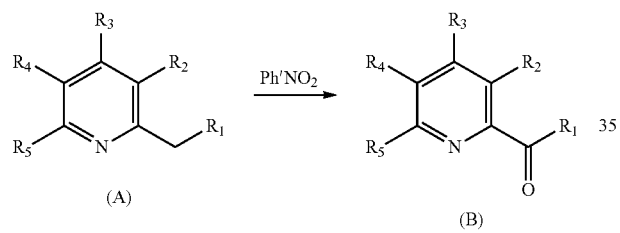

(A)  (B)

Preferably, said substituted phenyl group of the pyridine ring can be embodied as 2-methyl phenyl, 3-methyl phenyl, 4-methyl phenyl, 2,3-dimethyl phenyl, 2,4-dimethyl phenyl, 2,5-dimethyl phenyl, 2,6-dimethyl phenyl, 3,4-dimethyl phenyl, 3,5-dimethyl phenyl, 2,4,6-trimethyl phenyl, 4-bromo-2,6-dimethyl phenyl, 2-ethyl phenyl, 2-ethyl-6-methyl phenyl, 2-isopropyl phenyl, 2,6-diethyl phenyl, 2,6-diisopropyl phenyl, 2-fluorophenyl, 2-fluoro-4-methyl phenyl, 2-fluoro-5-methyl phenyl, 2,4-difluoro phenyl, 2,5-difluoro phenyl, 2,6-difluoro phenyl, 3,4-difluoro phenyl, 2,3,4-trifluoro phenyl, 2,4,5-trifluoro phenyl, 2,4,6-trifluoro phenyl, 2,3,4,5,6-pentafluoro phenyl, 3-chloro phenyl, 2,6-chloro phenyl, 2,3,4-trichloro phenyl, 2,4,5-trichloro phenyl, 2,4,6-trichloro phenyl, 2-bromo phenyl, 2-bromo-4-methyl phenyl, 2-bromo-4-fluoro phenyl, 4-bromo-2-fluoro phenyl, 2,6-dibromo phenyl, 2,6-dibromo-4-methyl phenyl, 2,6-dibromo-4-chloro phenyl, 2,4,6-tribromo phenyl, 2-bromo-6-chloro-4-fluoro phenyl, 2-bromo-4-chloro-6-fluoro phenyl, 2-bromo-4,6-difluoro phenyl, 3-nitro phenyl, 4-methoxy phenyl, 2-methyl-4-methoxy phenyl, or 4-ethoxy phenyl.

Wherein preferably, $R_1$ is selected from hydrogen, a methyl group, an ethyl group, a propyl group, a butyl group, a phenyl group and a substituted phenyl group, and $R_2$-$R_5$ can be selected from hydrogen, a methyl group, an ethyl group, a propyl group, a butyl group, a vinyl group, a propenyl group, a butenyl group, an ethynyl group, a propynyl group, a butynyl group, fluorine, chlorine, bromine, a methoxy group, an ethoxy group, a propoxy group, a nitro group, a phenyl group and a substituted phenyl group independently.

In another preferable embodiment of the present invention, said N ortho acyl substituted nitrogen-containing heterocyclic compound is substituted or unsubstituted 2,6-diacyl pyridine as shown in formula $B_1$, a compound as shown in formula $A_1$ reacts with a substituted or unsubstituted nitrobenzene to generate the compound as shown in formula $B_1$, wherein $R_1$ and $R_5'$ can be hydrogen, a $C_1$-$C_6$ alkyl group, a $C_2$-$C_6$ alkenyl or alkynyl group, a phenyl group or a substituted phenyl group independently, and $R_2$-$R_4$ can be hydrogen, a $C_1$-$C_6$ alkyl group, a $C_2$-$C_6$ alkenyl or alkynyl group, a halogen, a $C_1$-$C_6$ alkoxy group, a nitro group, a phenyl group or a substituted phenyl group independently; and the five substituent groups in the benzene ring of the substituted phenyl group can be a $C_1$-$C_6$ alkyl group, a $C_2$-$C_6$ alkenyl or alkynyl group, a halogen, a $C_1$-$C_6$ alkoxy group or a nitro group independently. For the preferred substituted phenyl in the pyridine ring, see the preferred substituted phenyl in the above-mentioned pyridine ring.

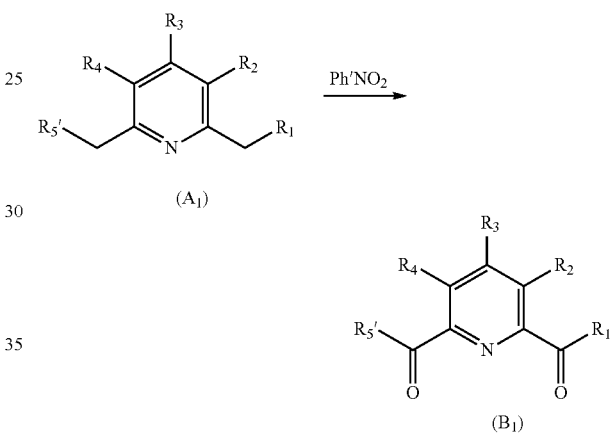

($A_1$)

($B_1$)

Wherein preferably, $R_1$ and $R_5'$ can be selected from hydrogen, a methyl group, an ethyl group, a propyl group, a butyl group, a phenyl group and a substituted phenyl group independently, and $R_2$-$R_4$ can be hydrogen, a methyl group, an ethyl group, a propyl group, a butyl group, a vinyl group, a propenyl group, a butenyl group, an ethynyl group, a propynyl group, a butynyl group, fluorine, chlorine, bromine, a methoxy group, an ethoxy group, a propoxy group, a nitro group, a phenyl group or a substituted phenyl group independently.

In the above embodiments, further preferably said N ortho acyl substituted nitrogen-containing heterocyclic compound is 2,6-diacetyl pyridine, 2,6-diethyl pyridine as shown in a formula I' reacts with a substituted or unsubstituted nitrobenzene to generate 2,6-diacetyl pyridine as shown in a formula b'.

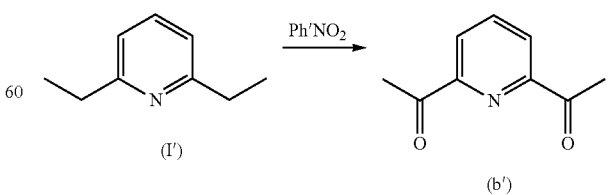

(I')

(b')

In another preferable embodiment of the present invention, wherein said the N ortho acyl substituted nitrogen-containing heterocyclic compound is a compound as shown in formula B', i.e., a compound as shown in formula A' reacts with a substituted or unsubstituted nitrobenzene to generate the compound as shown in formula B'; wherein $R_1$ is selected from hydrogen, a $C_1$-$C_6$ alkyl group, a $C_2$-$C_6$ alkenyl or alkynyl group, a phenyl group and a substituted phenyl group, and $R_2$-$R_3$ and $R_{11}$-$R_{14}$ can be hydrogen, a $C_1$-$C_6$ alkyl group, a $C_2$-$C_6$ alkenyl or alkynyl group, a halogen, a $C_1$-$C_6$ alkoxy group, a nitro group, a phenyl group or a substituted phenyl group independently; and the five substituent groups in the benzene ring of the substituted phenyl group can be a $C_1$-$C_6$ alkyl group, a $C_2$-$C_6$ alkenyl or alkynyl group, halogen, a $C_1$-$C_6$ alkoxy group or a nitro group independently. For the preferred substituted phenyl in the quinoline ring, see the preferred substituted phenyl in the above-mentioned pyridine ring.

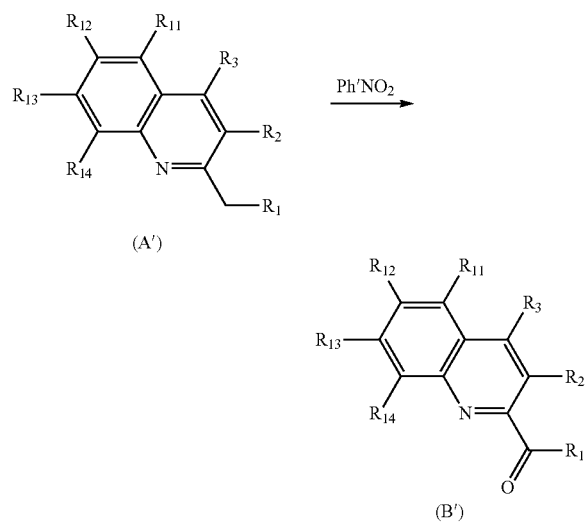

Wherein preferably, $R_1$ is selected from hydrogen, a methyl group, an ethyl group, a propyl group, a butyl group, a phenyl group and a substituted phenyl group, $R_2$-$R_3$ and $R_{11}$-$R_{14}$ can be selected from hydrogen, a methyl group, an ethyl group, a propyl group, a butyl group, a vinyl group, a propenyl group, a butenyl group, an ethynyl group, a propynyl group, a butynyl group, fluorine, chlorine, bromine, a methoxy group, an ethoxy group, a propoxy group, a nitro group, a phenyl group and a substituted phenyl group independently.

In another preferable embodiment of the present invention, said N ortho acyl substituted nitrogen-containing heterocyclic compound is a compound as shown in a formula $B_1''$, i.e., a compound as shown in a formula $A_1''$ reacts with a substituted or unsubstituted nitrobenzene to generate the compound as shown in formula $B_1''$; wherein $R_1$ and $R_{10}'$ can be hydrogen, a $C_1$-$C_6$ alkyl group, a $C_2$-$C_6$ alkenyl or alkynyl group, a phenyl group or a substituted phenyl group independently, and $R_2$-$R_3$ and $R_6$-$R_9$ can be hydrogen, a $C_1$-$C_6$ alkyl group, a $C_2$-$C_6$ alkenyl or alkynyl group, a halogen, a $C_1$-$C_6$ alkoxy group, a nitro group, a phenyl group or a substituted phenyl group independently; and the five substituent groups in the benzene ring of the substituted phenyl group can be a $C_1$-$C_6$ alkyl group, a $C_2$-$C_6$ alkenyl or alkynyl group, a halogen, a $C_1$-$C_6$ alkoxy group or a nitro group independently. For the preferred substituted phenyl in the phenanthroline ring, see the preferred substituted phenyl in the above-mentioned pyridine ring.

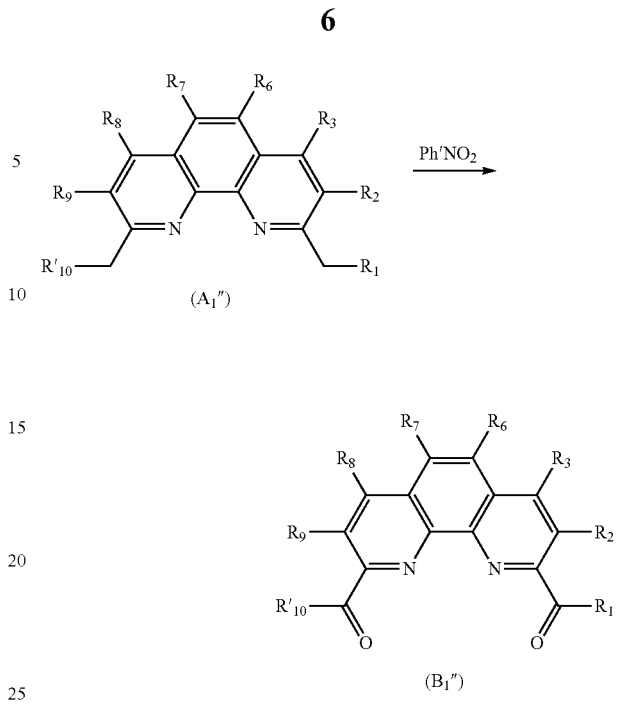

Wherein preferably, $R_1$ and $R_{10}'$ can be selected from hydrogen, a methyl group, an ethyl group, a propyl group, a butyl group, a phenyl group and a substituted phenyl group independently, and $R_2$-$R_3$ and $R_6$-$R_9$ can be selected from hydrogen, a methyl group, an ethyl group, a propyl group, a butyl group, a vinyl group, a propenyl group, a butenyl group, an ethynyl group, a propynyl group, a butynyl group, fluorine, chlorine, bromine, a methoxy group, an ethoxy group, a propoxy group, a nitro group, a phenyl group and a substituted phenyl group independently.

In another preferable embodiment of the present invention, said N ortho acyl substituted nitrogen-containing heterocyclic compound is a compound as shown in formula B", i.e., a compound as shown in formula A" reacts with a substituted or unsubstituted nitrobenzene to generate the compound as shown in formula B", wherein $R_1$ can be hydrogen, a $C_1$-$C_6$ alkyl group, a $C_2$-$C_6$ alkenyl or alkynyl group, a phenyl group or a substituted phenyl group independently, and $R_2$-$R_3$ and $R_6$-$R_{10}$ can be hydrogen, a $C_1$-$C_6$ alkyl group, a $C_2$-$C_6$ alkenyl or alkynyl group, a halogen, a $C_1$-$C_6$ alkoxy group, a nitro group, a phenyl group or a substituted phenyl group independently; and the five substituent groups in the benzene ring of the substituted phenyl group can be a $C_1$-$C_6$ alkyl group, a $C_2$-$C_6$ alkenyl or alkynyl group, a halogen, a $C_1$-$C_6$ alkoxy group or a nitro group independently. For the preferred substituted phenyl in the phenanthroline ring, see the preferred substituted phenyl in the above-mentioned pyridine ring.

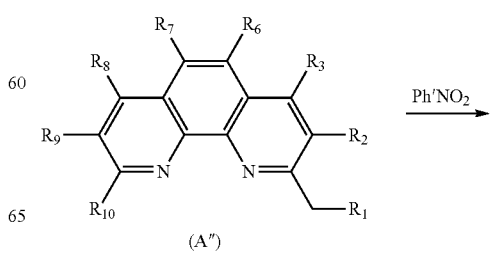

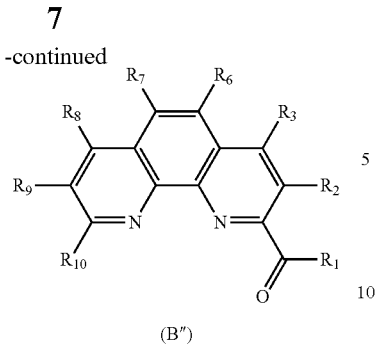

(B″)

Preferably, $R_1$ is selected from hydrogen, a methyl group, an ethyl group, a propyl group, a butyl group, a phenyl group and a substituted phenyl group, and $R_2$-$R_3$ and $R_6$-$R_{10}$ can be selected from hydrogen, a methyl group, an ethyl group, a propyl group, a butyl group, a vinyl group, a propenyl group, a butenyl group, an ethynyl group, a propynyl group, a butynyl group, fluorine, chlorine, bromine, a methoxy group, an ethoxy group, a propoxy group, a nitro group, a phenyl group and a substituted phenyl group independently.

In a specific example of the present invention, said N ortho acyl substituted nitrogen-containing heterocyclic compound is 2-acyl-1,10-phenanthroline, i.e., a compound as shown in formula I reacts with a substituted or unsubstituted nitrobenzene to generate 2-acyl-1,10-phenanthroline as shown in formula b, wherein R is a $C_1$-$C_6$ alkyl group, a benzyl group or a substituted benzyl group, R' is hydrogen or an alkyl group less than R by a $CH_2$, or a phenyl group or a substituted phenyl group, and when R is a substituted benzyl group, the five substituent groups in the benzene ring thereof can be a $C_1$-$C_6$ alkyl group, a $C_2$-$C_6$ alkenyl or alkynyl group, a halogen, a $C_1$-$C_6$ alkoxy group or a nitro group independently.

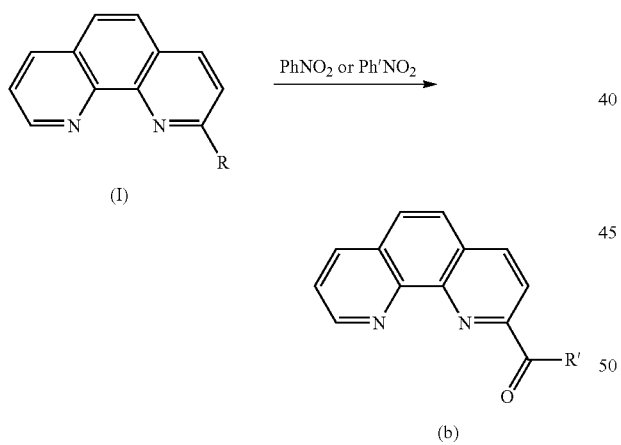

In the above method for the synthesis of 2-acyl-1,10-phenanthroline, the oxidation reaction is preferably carried out at a temperature of 200~220° C. under reflux, and the oxidation reaction time is 10 to 100 h, preferably 24 to 60 h. The molar ratio of the compound as shown in formula I to substituted or unsubstituted nitrobenzene is 1:0.5 to 1:30, preferably 1:5 to 1:20. In the above method, preferably, R in the compound as shown in formula I is a methyl, an ethyl, a propyl, a butyl or a benzyl group, then the corresponding R' would be hydrogen, a methyl group, an ethyl group, an n-propyl group, an isopropyl group or a benzyl group.

In the method for the synthesis of 2-acyl-1,10-phenanthroline of the present invention, wherein in a specific example, said compound as shown in formula I is prepared by the following steps, reacting 1,10-phenanthroline with trialkyl aluminum, or a halogenoalkyl aluminum $R_nAlX_m$, or a substituted or unsubstituted benzyl lithium Ph'CH$_2$Li, followed by hydrolysis and oxidation to obtain the compound as shown in formula I. In halogenoalkyl aluminum $R_nAlX_m$, R can be the same or different $C_1$-$C_6$ alkyl groups, X is a halogen, $1 \leq n \leq 3$, $0 \leq m \leq 2$, and m+n=3.

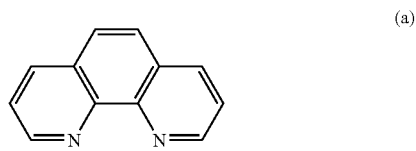

(a)

In said specific example, the halogenoalkyl aluminum $R_nAlX_m$ is preferably one or more selected from the group consisting of trimethyl aluminum, triethyl aluminum, trinpropyl aluminum, trin-butyl aluminum, triiso-butyl aluminum, trin-hexyl aluminum, trin-octyl aluminum, diethyl aluminum chloride, and ethyl aluminum dichloride, further preferably triethyl aluminum. Wherein said hydrolysis is carried out in water or alcohol, preferably in water.

In said specific example, the molar ratio of 1,10-phenanthroline to $R_nAlX_m$ or Ph'CH$_2$Li is preferably 1:0.5 to 1:4.5, more preferably 1:2.0 to 1:2.6; the reaction temperature of 1,10-phenanthroline with $R_nAlX_m$ or Ph'CH$_2$Li is preferably −60 to −80° C., more preferably −60 to −70° C., which is raised to 20 to 40° C. after reacting for a period of time, and then the reaction is continued. In addition, the hydrolysis temperature is preferably −60 to 0° C.

The present invention also provides a preparation method for 2-acyl-1,10-phenanthroline aminal iron (II) chloride complex as shown in formula II, wherein the raw material 2-acyl-1,10-phenanthroline as shown in formula b is prepared according to the above method of the present invention, and in formula II, R″ is a substituted or unsubstituted phenyl, a 1-naphthyl or a diphenylmethyl group; and when R″ is a substituted phenyl group, the five substituent groups in the benzene ring thereof can be hydrogen, a $C_1$-$C_6$ alkyl group, a $C_2$-$C_6$ alkenyl or alkynyl group, a halogen, a $C_1$-$C_6$ alkoxy group or a nitro group independently.

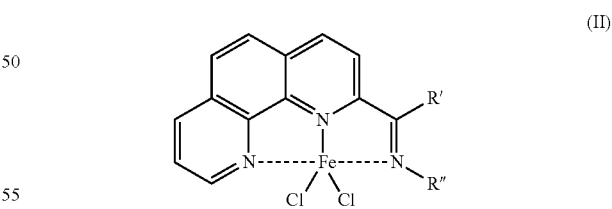

(II)

In a specific example of the preparation method for the complex as shown in formula II in the present invention, the complex as shown in formula II is prepared by 2-acyl-1,10-phenanthroline as shown in formula b through step B and step C. In step B the compound as shown in formula b reacts with arylamines R″NH2 as shown in formula c in a strong organic acid to generate a compound as shown in formula d, and in step C a compound as shown in formula d reacts with ferrous chloride to generate 2-acyl-1,10-phenanthroline aminal iron (II) chloride complex as shown in formula II.

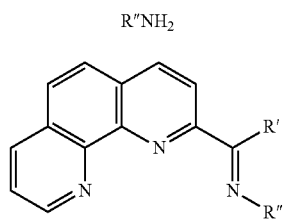

(c)

R"NH2

(d)

In the above example, the strong organic acid is preferably p-toluenesulfonic acid, formic acid, acetic acid, propionic acid, butyric acid, benzoic acid, naphthenic acid or benzyl acid, more preferably p-toluenesulfonic acid, and the molar ratio of the compound as shown in formula b to arylamines R"NH2 as shown in formula c is preferably 1:1 to 1:5.

In the above example, when R" is a substituted phenyl group, the arylamines R"NH2 as shown in formula c is one or more selected from the group consisting of 2-methyl aniline, 3-methyl aniline, 4-methyl aniline, 2,3-dimethyl aniline, 2,4-dimethyl aniline, 2,5-dimethyl aniline, 2,6-dimethyl aniline, 3,4-dimethyl aniline, 3,5-dimethyl aniline, 2,4,6-trimethyl aniline, 4-bromo-2,6-dimethyl aniline, 2-ethyl aniline, 2-ethyl-6-methyl aniline, 2-isopropyl aniline, 2,6-diethyl aniline, 2,6-diisopropyl aniline, 2-fluoroaniline, 2-fluoro-4-methyl aniline, 2-fluoro-5-methyl aniline, 2,4-difluoroaniline, 2,5-difluoroaniline, 2,6-difluoroaniline, 3,4-difluoroaniline, 2,3,4-trifluoroaniline, 2,4,5-trifluoroaniline, 2,4,6-trifluoroaniline, 2,3,4,5,6-pentafluoroaniline, 3-chloroaniline, 2,6-chloroaniline, 2,3,4-trichloroaniline, 2,4,5-trichloroaniline, 2,4,6-trichloroaniline, 2-bromoaniline, 2-bromo-4-methyl aniline, 2-bromo-4-fluoro aniline, 4-bromo-2-fluoro aniline, 2,6-dibromoaniline, 2,6-dibromo-4-methyl aniline, 2,6-dibromo-4-chloro aniline, 2,4,6-tribromoaniline, 2-bromo-6-chloro-4-fluoro aniline, 2-bromo-4-chloro-6-fluoro aniline, 2-bromo-4,6-difluoro aniline, 3-nitroaniline, 4-methoxyaniline, 2-methyl-4-methoxy aniline and 4-ethoxyaniline. More preferably, the arylamine R"NH2 as shown in formula c is 2,6-diethyl aniline.

In the above method, said step B and step C are carried out in an organic solvent, and said organic solvent is one or more selected from the group consisting of toluene, cyclohexane, diethyl ether, tetrahydrofuran, ethanol, benzene, xylene and dichloromethane, wherein toluene is preferred in step B, and tetrahydrofuran is preferred in step C.

The present invention also provides the use of 2-acyl-1,10-phenanthroline aminal iron (II) chloride complex prepared according to the above process of the present invention in ethylene oligomerization catalyst.

In the present invention, the term "$(C_1\text{-}C_6)$ alkyl group" refers to a saturated straight chain or branched chain alkyl group with 1-6 carbon atoms. Said $(C_1\text{-}C_6)$ alkyl group includes methyl, ethyl, n-propyl, isopropyl, n-butyl, isobutyl, sec-butyl, tert-butyl, n-pentyl, isopentyl, sec-pentyl, n-hexyl, 2-methyl pentyl, 3-methyl pentyl, 2,3-dimethyl butyl and 2,2-dimethyl butyl group, preferably methyl, ethyl, n-propyl or isopropyl group.

In the present invention, the term "$C_2\text{-}C_6$ alkenyl or alkynyl group" refers to an unsaturated straight chain or branched chain hydrocarbyl group with 2-6 carbon atoms. Said $C_2\text{-}C_6$ alkenyl or alkynyl group includes vinyl, 1-methyl vinyl, 2-methyl vinyl, 2-ethyl vinyl, 2,2-dimethyl vinyl, 1,2-dimethyl vinyl, 2-propyl vinyl, 3-methyl butenyl, 2-methyl butenyl, 1-methyl butenyl, 1,2-dimethyl propenyl, 2-butyl vinyl, 4-methyl pentenyl, 3-methyl pentenyl, 2-methyl pentenyl, 1-methyl pentenyl, 2,3-dimethyl butenyl, 1,3-dimethyl butenyl, 1,2-dimethyl butenyl, 3,3-dimethyl butenyl, ethynyl, propynyl, butynyl, 2-propyl ethynyl, 3-methyl butynyl, 2-butyl ethynyl, 4-methyl pentynyl and 3-methyl pentynyl group, preferably vinyl, 1-methyl vinyl or 2-ethyl vinyl group.

In the present invention, the term "$(C_1\text{-}C_6)$ alkoxyl group" refers to the group obtained from the bond of a $(C_1\text{-}C_6)$ alkyl group with an oxygen atom. Said $(C_1\text{-}C_6)$ alkoxyl group includes methoxy, ethoxy, n-propoxy, isopropoxy, n-butoxy, isobutoxy, sec-butoxy, tert-butoxy, n-pentoxy, sec-pentoxy, n-hexyloxy and sec-hexyloxy group, preferably methoxy or ethoxy group.

In the present invention, the term "halogen" includes fluorine, chlorine, bromine and iodine, preferably fluorine, chlorine or bromine.

In the present invention, the five substituents in the above benzene ring can be preferably selected from hydrogen, a methyl group, an ethyl group, an n-propyl group, an isopropyl group, fluorine, chlorine, bromine, a methoxy group, an ethoxy group, and a nitro group.

In the present invention, the process for preparing 2-acyl-1,10-phenanthroline as shown in formula b by 1,10-phenanthroline as shown in formula a is named as step A. In a specific embodiment of the present invention, 1,10-phenanthroline reacts with trialkyl aluminum or benzyl Li in the presence of an organic solvent to prepare 2-acyl-1,10-phenanthroline as shown in formula b. The organic solvent used for this is one or more selected from the group consisting of toluene, cyclohexane, diethyl ether, tetrahydrofuran, ethanol, benzene, dimethyl benzene and dichloromethane, preferably toluene. Such organic solvents are used to prepare a solution of 1,10-phenanthroline, wherein the content of solution is 10 to 200 g/L. The reaction of said 1,10-phenanthroline with triethyl aluminum or benzyl Li is commonly carried out at a temperature form −60 to −80° C., preferably from −60 to −70° C. In addition, the reaction is preferably carried out under an inert atmosphere, and the inert atmosphere is preferably argon or nitrogen. Anhydrous 1,10-phenanthroline or hydrated 1,10-phenanthroline can be used as 1,10-phenanthroline, wherein anhydrous 1,10-phenanthroline is preferred. Trialkyl aluminum or benzyl Li can be used as itself. The molar ratio of 1,10-phenanthroline to trialkyl aluminum or benzyl Li is 1:0.5 to 1:4.5, preferably 1:2.0 to 1:2.6. Advantageously, trialkyl aluminum or benzyl Li is commonly added into the solution of 1,10-phenanthroline at the reaction temperature in the reaction, such as adding dropwise trialkyl aluminum or benzyl Li. After the addition is completed, the reaction mixture is stirred at the reaction temperature for 18 to 28 h, preferably 18 to 20 h. After that, raising the temperature of the reaction mixture to a range of 20 to 40° C. and stirring it for 5 to 10 h, preferably 10 h so as to ensure a complete reaction. Then water is added for hydrolysis at −60 to 0° C., and deionized water is preferred. For example, the reaction mixture is kept at −30° C., and then water is added for hydrolysis. In the hydrolysis, bubbles come up, and the hydrolysis reaction continues carried out until no bubble comes out. In order to hydrolyze completely, the temperature of reaction mixture is raised to a range of 20 to 40° C. and stirred for 5 to 10 h, the liquid is separated, and the organic phase is taken out. In order to separate the desired products as many as possible, it is preferably to extract the inorganic phase by an organic solvent, and the obtained organic phase is combined with the organic phase obtained by the above separation. The used organic solvent can be ethyl acetate, acetone, dichloromethane, or a mixture thereof, preferably dichloromethane. After removing the solvent in the organic phase or combined organic phase under reduced pressure, nitrobenzene is added at 200 to 220° C. (such as 210° C.) for reflux extraction for 10 to 100 h, preferably 15 to 24 h. Then after filtration, the nitrobenzene solvent is removed under reduced pressure. The mixture solution of ethyl acetate and petroleum ether with a volume ratio of 1:1 to 1:5, preferably 1:2, is used as an eluent to conduct silica gel column chromatography, and a solid product is obtained, i.e. the compound as shown in formula b. In the synthesis step, the molar ratio of 1,10-phenanthroline to nitrobenzene is 1:0.5 to 1:30, preferably 1:5 to 1:20.

In the specific embodiment, in step B, i.e. the synthesis of 2-acyl-1,10-phenanthroline aminal ligand, the compound as shown in formula b reacts with the compound as shown in formula c in the presence of p-toluenesulfonic acid as a catalyst to obtain the compound as shown in formula d.

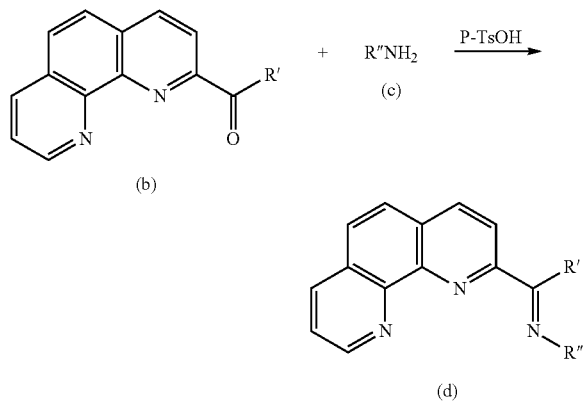

Ligand d is prepared in a vessel by reacting 2-acyl-1,10-phenanthroline obtained by step A with substituted aniline, 1-naphthylamine or dibenzyl methylamine as shown in formula c in an organic solvent without water and oxygen, wherein the molar ratio of 2-acyl-1,10-phenanthroline to substituted aniline, 1-naphthylamine or dibenzyl methylamine as shown in formula c is 1:1 to 1:5. The used organic solvent can be selected from toluene, cyclohexane, diethyl ether, tetrahydrofuran, ethanol, benzene, xylene, dichloromethane, or a mixture thereof, preferably toluene. The reaction is carried out under reflux with p-toluenesulfonic acid (p-TsOH) as a catalyst, for example at 110° C. The weight ratio of p-toluenesulfonic acid to the total reactants is 0.001:1 to 0.02:1, and the reaction time is 5 to 10 h. The reaction is detected by TLC. After 2-acyl-1,10-phenanthroline is reacted completely, the solvent is removed under reduced pressure. Then the mixed solution of ethyl acetate and petroleum ether with a volume ratio of 1:1 to 1:9, preferably 1:4, is used as an eluent to conduct silica gel column chromatography, and the object product is obtained, i.e. the compound as shown in formula d. The object product is characterized by Nuclear Magnetic Resonance and Mass Spectrometry.

In the specific embodiment, in step C, i.e. the synthesis of 2-acyl-1,10-phenanthroline aminal iron (II) chloride complex, the compound as shown in formula d reacts with ferrous chloride to obtain the compound as shown in formula II, i.e. 2-acyl-1,10-phenanthroline aminal iron (II) chloride complex.

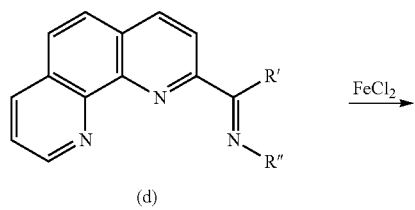

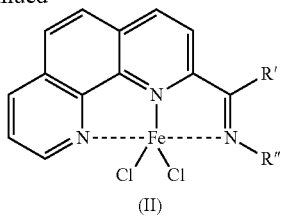

Ferrous chloride is dissolved in an organic solvent without water and oxygen under an inert gas atmosphere such as nitrogen to form ferrous chloride solution of 0.01-0.1g/ml, and the used solvent therein can be selected from toluene, cyclohexane, diethyl ether, tetrahydrofuran, ethanol, benzene, xylene, dichloromethane, or a mixture thereof, preferably tetrahydrofuran. Hydrated ferrous chloride ($FeCl_2 \cdot 4H_2O$) can be used to replace ferrous chloride to obtain the above solution of ferrous chloride. 2-acyl-1,10-phenanthroline aminal ligand d is separately dissolved in an organic solvent without water and oxygen to form a solution of 0.01 to 0.1 g/ml, and the solvent can also be selected from toluene, cyclohexane, diethyl ether, tetrahydrofuran, ethanol, benzene, xylene, dichloromethane, or a mixture thereof, preferably tetrahydrofuran. The above two solutions are combined under an inert gas such as nitrogen (for example, at room temperature), and the mixture is then stirred at room temperature under an inert gas, such as nitrogen, for a certain time, such as being stirred for a night at room temperature. The reaction is detected by TLC. After the reaction is completed, after-treatment is made to the reaction product by common after-treatment methods such as suction filtration, washing and drying, and then the complex as shown in formula II is obtained. The organic solvent such as anhydrate diethyl ether can be used for washing. The complex is characterized by Nuclear Magnetic Resonance and Mass Spectrometry. In said synthesis step, the molar ratio of 2-acyl-1,10-phenanthroline aminal ligand d to ferrous chloride is 1:1 to 1.2:1, preferably 1.05:1 to 1.1:1.

The 2-acyl-1,10-phenanthroline aminal iron (II) chloride complex prepared by the present invention can be used as an oligomerization catalyst for olefin oligomerization, particularly for ethylene oligomerization. The related oligomerization conditions are well-known for one skilled in the art, for example, the ethylene oligomerization process under pressure described in CN1850339A can be used for oligomerization. Said document is introduced herein by reference. For example, according to the present invention, ethylene oligomerization can be carried out as follows. An organic solvent, a cocatalyst and 2-acyl-1,10-phenanthroline aminal iron (II) chloride complex prepared by the present invention as the main catalyst are added into the reactor. Then the reaction is carried out at an ethylene pressure of 0.1-30 MPa and a temperature of 20-150° C. for 30-100 min, and the ethylene oligomerization product is obtained. Then it is cooled to a range of −10 to 10° C., a small amount of oligomerization product is taken out, neutralized by dilute hydrochloric acid of 5%, and analyzed by Gas Chromatography (GC).

When the 2-acyl-1,10-phenanthroline aminal iron (II) chloride complex prepared according to the present invention is used as the main catalyst for ethylene oligomerization, a cocatalyst should be used in addition of the above main cata lyst. A compound selected from aluminoxane compounds, alkyl aluminum compounds, and so on, can be used as a cocatalyst. Aluminoxane compounds can be $C_1$-$C_4$ alkyl aluminoxanes, wherein $C_1$-$C_4$ alkyl groups are straight chains or branched chains. The examples of aluminoxanes that can be used include methyl aluminoxane, modified methyl aluminoxane, ethyl aluminoxane, isobutyl aluminoxane, and so on, preferably methyl aluminoxane. Alkyl aluminum compounds can be shown by formula $AlR_nX_m$, wherein R can be a straight chain or a branched chain $C_1$-$C_8$ alkyl group independently, X is a halogen, preferably chlorine or bromine, $1 \leq n \leq 3$, $0 \leq m \leq 2$, and $m+n=3$. The examples of alkyl aluminum compounds that can be used include trimethyl aluminum, triethyl aluminum, triiso-butyl aluminum, trin-hexyl aluminum, trin-octyl aluminum, diethyl aluminum chloride, ethyl aluminum dichloride, and so on, preferably triethyl aluminum.

The organic solvent used in ethylene oligomerization of the present invention is selected from toluene, cyclohexane, diethyl ether, tetrahydrofuran, ethanol, benzene, xylene, dichloromethane, and so on, preferably toluene. When the main catalyst prepared by the present invention and the cocatalyst are used for ethylene oligomerization, preferably, the temperature of oligomerization reaction is commonly 20-80° C., the pressure thereof is 1-5 MPa, and the reaction time is advantageously 30-60 min.

Using the 2-acyl-1,10-phenanthroline aminal iron (II) chloride complex prepared in the present invention for ethylene oligomerization, the obtained ethylene oligomerization products include $C_4$ olefins, $C_6$ olefins, $C_8$ olefins, $C_{10}$ olefins, $C_{12}$ olefins, $C_{14}$ olefin, $C_{16}$ olefins, $C_{18}$ olefins, $C_{20}$ olefins, $C_{22}$ olefins and so on, and the selectivity of alpha olefins can reach 96% or higher. After the ethylene oligomerization is completed, a small amount of reaction mixture is taken out, neutralized by 5% dilute hydrochloric acid, and analyzed by Gas Chromatography (GC). The result shows that the oligomerization activity is high. In addition, the residual reaction mixtures are neutralized by ethanol solution which is acidified by dilute hydrochloric acid of 5%, only small amount of polymers are formed when an aluminoxane is used as the cocatalyst, but no polymer is formed when an alkyl aluminum compound is used as the cocatalyst.

The present invention possesses the following advantages when compared with the prior art: using nitrobenzene instead of selenium dioxide to prepare 2-acyl-1,10-phenanthroline by oxidation has the advantages of simple process, a low toxic effect and a reduced cost of the catalyst. In addition, compared with the process of using potassium cyanide to prepare 2-acyl-1,10-phenanthroline in the prior art, alkyl aluminum or benzyl Li with low toxic or of non-toxic are used for nucleophilic substitution reaction, and nitrobenzene is used for oxidation reaction in the present invention, which also has the advantages of few synthetic steps, an easy process and a low toxic effect and a reduced preparation costs of the catalyst, and has a promising outlook in industrial application.

EMBODIMENT

The present invention will be explained in detail by the following examples. Obviously, these examples do not restrict the scope of the present invention in any manner. Changes or amendment made without departing from the scope and spirit of the present invention, are within the scope of the appended claims.

Example 1

1. Synthesis of the Catalyst 2-n-butyryl-1,10-phenanthroline (2,6-diethylanil) iron (II) Chloride Complex
Step A. Synthesis of 2-n-butyryl-1,10-phenanthroline

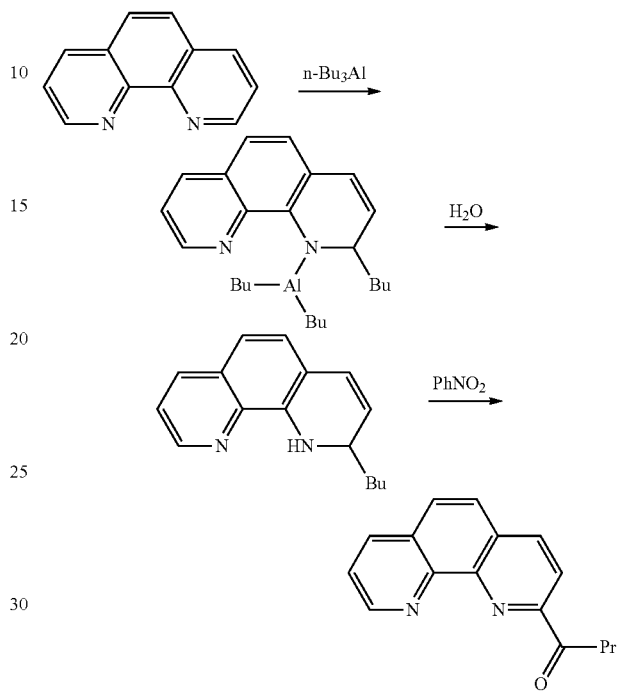

5.1 g of 1,10-phenanthroline (28.3 mmol) is added into 250 ml of three-necked flask, and dissolved in 100 ml of toluene under nitrogen and magnetic stirring. 13.7 ml of trin-butyl aluminum (d=0.82 g/ml, 56.6 mmol) is added slowly and dropwise into the three-necked flask under stirring at −60° C. within about 15 min, and the mixture is stirred for 18 h at −60° C. The temperature is raised to about 30° C., and the stirring is continued for 10 h. Then the reaction mixture is cooled to about −30° C., and 50 ml of distilled water is added into it slowly, then the temperature is raised to 30° C. and the stirring for 10 h. Then the mixture is separated and the organic phase is taken out, and the inorganic phase is extracted by dichloromethane for 3 times, the amount of dichloromethane being 20 ml each time, and the organic phases are combined. The solvent in the combined organic phase is removed under reduced pressure, and 50 ml of nitrobenzene (1.205 g/ml) is added, which is then refluxed at 210° C. for about 58 h. After filtration, nitrobenzene is removed at a pressure lower than 10 mmHg, and a black viscous liquid substance is obtained. The mixed solution of ethyl acetate and petroleum ether with a volume ratio of 1:2 is used as an eluent to make silica gel column chromatography on the black viscous liquid substance, and a brown product is obtained with a weight of 2.1 g and a yield of 30%. The product is identified as 2-n-butyryl-1,10-phenanthroline by Nuclear Magnetic Resonance and Mass Spectrometry.

Mass Spectrometry MS-EI: 250.
Nuclear Magnetic Resonance analysis, $^1$H NMR(400 MHz, CDCl$_3$): δ9.26(dd, J=1.72, 1H); 8.33(s, 2H); 8.27(dd, J=1.68, 1H); 7.86(d, J=8.8, 1H); 7.80(d, J=8.8, 1H); 7.68(dd, J=5.28, 1H); 3.67(t, J=7.24, 2H); 1.89(m, J=7.4, 2H); 1.10(t, J=7.4, 3H).

Step B: Synthesis of 2-n-butyryl-1,10-phenanthroline (2,6-diethylanil) Ligand

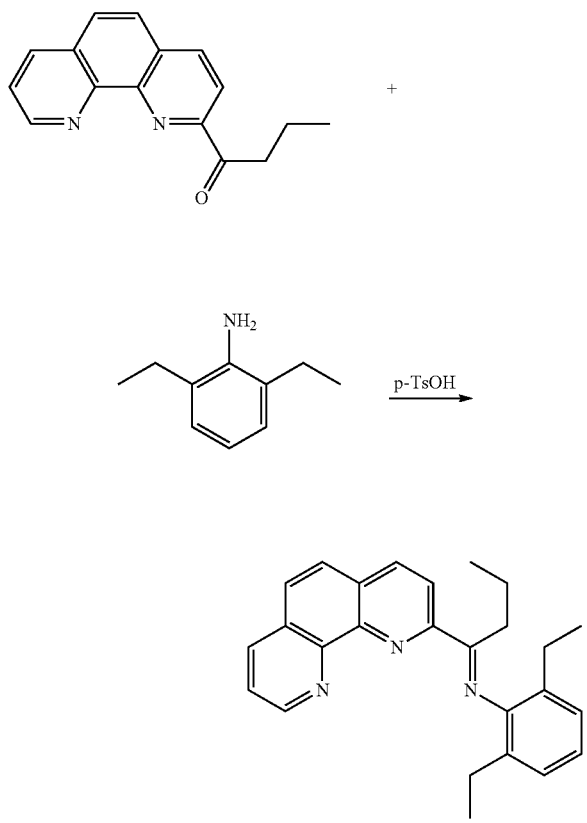

Into a 100 ml two-necked flask equipped with a water separator, 0.53 ml of 2-n-butyryl-1,10-phenanthroline (2.12 mmol) obtained in step A, 0.95 g of 2,6-diethyl aniline (6.36 mmol) and 35 ml of toluene without water or oxygen are added, wherein the molar ratio of 2-n-butyryl-1,10-phenanthroline to 2,6-diethyl aniline is 1:3. The water separator is equipped with a condenser tube. 0.01 g of p-toluenesulfonic acid is added, and refluxed at 110° C. for 6 h. After the removal of the solvent at reduced pressure, a mixed solution of ethyl acetate and petroleum ether with a volume ratio of 1:4 is used as an eluent, and a luminous yellow product with a weight of 0.65 g and a yield of 81% is obtained after silica gel column chromatography. The product is identified as 2-n-butyryl-1,10-phenanthroline (2,6-diethylanil) ligand by Nuclear Magnetic Resonance, Mass Spectrometry and Elemental analysis.

Mass Spectrometry MS-EI: 381.

Nuclear Magnetic Resonance analysis, $^1$H NMR(400 MHz, CDCl$_3$): δ9.25 (dd, J=2.96, 1H); 8.66(d, J=8.36, 1H); 8.33(d, J=8.36, 1H); 8.28(dd, J=7.84, 1H); 7.85(dd, J=9.02, 2H); 7.65(dd, J=4.36, 1H); 7.15(d, J=7.52, 2H); 7.06 (t, J=7.04, 1H); 3.01(t, J=7.84, —CNCH$_2$CH$_2$CH$_3$, 2H); 2.40 (m, J=7.52, phCH$_2$CH$_3$, 2H); 1.58(m, J=7.44, CH$_3$CH$_2$CH$_2$—, 2H); 1.20(t, J=7.30, phCH$_2$CH$_3$, 6H); 0.90 (t, J=7.32, CH$_3$CH$_2$CH$_2$—,3H).

Element analysis: C$_{26}$H$_{27}$N$_3$ (381.51), theoretical values: C, 81.85; H, 7.13; N, 11.01; measured values: C, 81.36; H, 7.23; N, 10.55.

Step C; Synthesis of 2-n-butyryl-1,10-phenanthroline (2,6-diethylanil) iron (II) Chloride

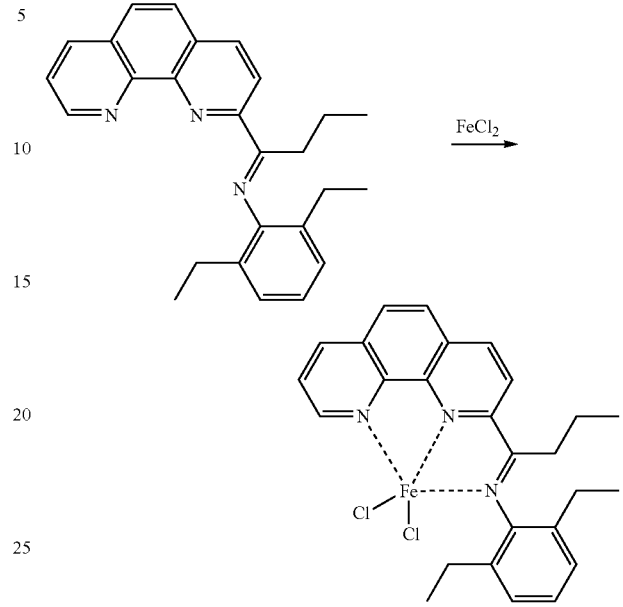

0.16 g of ferrous chloride (1.25 mmol) is dissolved by 20 ml of tetrahydrofuran without water and oxygen in a two-necked flask under nitrogen. 0.52 g of 2-n-butyryl-1,10-phenanthroline (2,6-diethylanil) ligand (1.36 mmol) obtained in step B is separately dissolved in 20 ml of tetrahydrofuran without water and oxygen. The above two solutions are combined at room temperature under nitrogen, when reaction occurs immediately, and the solution shows grayish black. The solution is stirred over night at room temperature under nitrogen. The reaction is detected by TLC until 2-n-butyryl-1,10-phenanthroline (2,6-diethylanil) ligand disappears basically.

After suction filtration, anhydrous diethyl ether is used for washing, and a silver-gray solid is obtained after vacuum drying. The solid is confirmed as 2-n-butyryl-1,10-phenanthroline (2,6-diethylanil) iron (II) chloride.

Element analysis: C$_{26}$H$_{27}$Cl$_2$FeN$_3$ (508.26), theoretical values: C, 61.44; H, 5.35; N, 8.27; measured values: C, 61.79; H, 5.60; N, 8.13.

2. Ethylene Oligomerization

Toluene, 1.33 ml of toluene solution (1.5 mol/l) of methyl aluminoxane (2.0 mmol) and 8 ml of toluene solution of the main catalyst 2-n-butyryl-1,10-phenanthroline (2,6-diethylanil) iron (II) chloride are added into a 300 ml stainless autoclave, wherein the total volume of the reactants is 100 ml, and the molar ratio of Al to Fe is 1000. When the polymerization temperature reaches 40° C., ethylene is fed into the reactor. The ethylene pressure is kept at 1 MPa and the reaction is carried out for 30 min under stirring. Then a small amount of the mixture is taken out by a syringe, and after being neutralized by 5% dilute hydrochloric acid, it is analyzed by GC. The result shows that the oligomerization activity is 2.73×10$^7$ g·mol$^{-1}$ (Fe)·h$^{-1}$, and the oligomer contents are respectively as follow, C$_4$: 25.51%, C$_6$~C$_{10}$: 55.23%, C$_6$-C$_{18}$: 70.82% (wherein 96.6% liner alpha olefins are contained), C$_{20}$-C$_{28}$: 3.67%, and the K value is 0.62. The residual reaction mixtures are neutralized by ethanol solution which is acidified by 5% dilute hydrochloric acid, and white waxy polymers are obtained, wherein the polymerization activity is 4.05×10$^4$ g·mol$^{-1}$(Fe)·h$^{-1}$.

Examples 2-47

The three steps A, B and C of Example 1 are repeated to prepare the catalyst, except that the 2,6-diethyl aniline in step B of Example 1 is substituted by the following substituted anilines successively, 2-methyl aniline, 3-methyl aniline, 4-methyl aniline, 2,3-dimethyl aniline, 2,4-dimethyl aniline, 2,5-dimethyl aniline, 2,6-dimethyl aniline, 3,4-dimethyl aniline, 3,5-dimethyl aniline, 2,4,6-trimethyl aniline, 4-bromo-2,6-dimethyl aniline, 2-ethyl aniline, 2-ethyl-6-methyl aniline, 2-isopropyl aniline, 2,6-diisopropyl aniline, 2-fluoroaniline, 2-fluoro-4-methyl aniline, 2-fluoro-5-methyl aniline, 2,4-difluoroaniline, 2,5-difluoroaniline, 2,6-difluoroaniline, 3,4-difluoroaniline, 2,3,4-trifluoroaniline, 2,4,5-trifluoroaniline, 2,4,6-trifluoroaniline, 2,3,4,5,6-pentafluoroaniline, 3-chloroaniline, 2,6-dichloroaniline, 2,3,4-trichloroaniline, 2,4,5-trichloroaniline, 2,4,6-trichloroaniline, 2-bromoaniline, 2-bromo-4-methyl aniline, 2-bromo-4-fluoroaniline, 4-bromo-2-fluoroaniline, 2,6-dibromoaniline, 2,6-dibromo-4-methyl aniline, 2,6-dibromo-4-chloroaniline, 2,4,6-tribromoaniline, 2-bromo-6-chloro-4-fluoroaniline, 2-bromo-4-chloro-6-fluoroaniline, 2-bromo-4,6-difluoro aniline, 3-nitroaniline, 4-methoxyaniline, 2-methyl-4-methoxy aniline, and 4-ethoxy aniline. The corresponding 2-n-butyryl-1,10-phenanthroline aminal ligands are obtained by 2-n-butyryl-1,10-phenanthroline and the above substituted anilines in step B, each of such ligand products being confirmed by Nuclear Magnetic Resonance, Mass Spectrometry and Elemental analysis, and the corresponding complexes of the above 2-n-butyryl-1,10-phenanthroline aminal ligands and ferrous chloride are obtained in step C, each of such complexes being confirmed by Elemental analysis.

Example 48

Step A in Example 1 is repeated. Step B in Example 1 is also repeated, except that 2,6-diethyl aniline is substituted by 1-naphthylamine, 2-n-butyryl-1,10-phenanthroline (1-naphthylanil) ligand is obtained, and the ligand is confirmed by Magnetic Resonance and Mass Spectrometry. Step C in Example 1 is repeated, except that 2-n-butyryl-1,10-phenanthroline (2,6-diethylanil) ligand is substituted by 2-n-butyryl-1,10-phenanthroline 1-naphthylanil ligand, 2-n-butyryl-1,10-phenanthroline (1-naphthylanil) iron (II) chloride is obtained, and the complex is confirmed by Elemental analysis.

Example 49

Step A in Example 1 is repeated. The step B in Example 1 is also repeated, except that the 2,6-diethyl aniline is substituted by diphenyl methylamine, 2-n-butyryl-1,10-phenanthroline (diphenyl methylanil) ligands are obtained, and the ligands are confirmed by Magnetic Resonance and Mass Spectrometry. Step C in Example 1 is repeated, except that 2-n-butyryl-1,10-phenanthroline (2,6-diethylanil) ligand is substituted by 2-n-butyryl-1,10-phenanthroline (diphenyl methylanil) ligand, 2-n-butyryl-1,10-phenanthroline (diphenyl methylanil) iron (II) chloride is obtained, and the complex is confirmed by Elemental analysis.

Example 50

1. Synthesis of the Catalyst 2-acetyl-1,10-phenanthroline (2,6-diethylanil) iron (II) Chloride Complex
Step A: Synthesis of 2-acetyl-1,10-phenanthroline

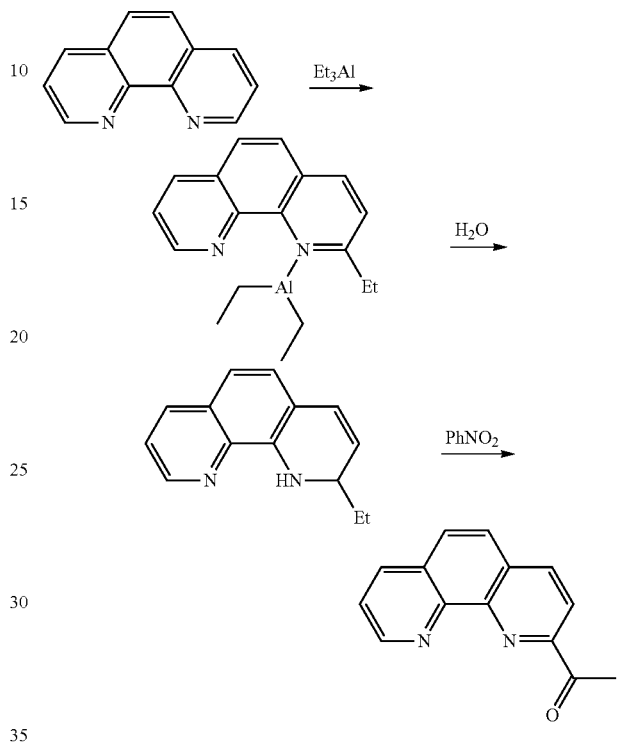

5.1 g of 1,10-phenanthroline (28.3 mmol) is fed into a 250 ml three-necked flask, and dissolved by using 100 ml of toluene under nitrogen and magnetic stirring. 10 ml of triethyl aluminum (70.8 mmol) is added slowly and dropwise into the three-necked flask under stirring at −60° C. within about 15 min, the stirring is continued for 18 h at −60° C., the temperature is raised to about 30° C., and the stirring is continued for 10 h. Then the reaction mixture is cooled to about −30° C., and 50 ml of distilled water is added into it slowly. Then the temperature is raised to 30° C. and the mixture is stirred for 10 h. The mixture is separated, wherein the organic phase is taken out, and the inorganic phase is extracted by dichloromethane for 3 times, the amount of dichloromethane being 20 ml each time, and the organic phases are combined. The solvent in the combined organic phase is removed under reduced pressure, and 50 ml of nitrobenzene (1.205 g/ml) is added, which is then refluxed at 210° C. for about 48 h. After filtration, nitrobenzene is removed at a pressure lower than 10 mmHg, and a black viscous liquid substance is obtained. The mixed solution of ethyl acetate and petroleum ether with a volume ratio of 1:2 as an eluent is used to make silica gel column chromatography on the black viscous liquid substance, and a brown product is obtained with a weight of 1.9 g and a yield of 30%. The product is identified as 2-acetyl-1,10-phenanthroline by Nuclear Magnetic Resonance and Mass Spectrometry.

Mass Spectrometry MS-EI: 222.

Nuclear Magnetic Resonance analysis, $^1$H NMR (400 MHz, CDCl$_3$): δ9.26 (d, J=3.9 Hz, 1H); 8.37(s, 2H); 8.29(d, J=8.1 Hz, 1H); 8.7(dd, J=8.7 Hz, 2H); 7.69(dd, J=7.8 Hz, 1H); 3.09 (s, 3H, CH3).

Step B: Synthesis of 2-acetyl-1,10-phenanthroline (2,6-diethylanil) Ligand

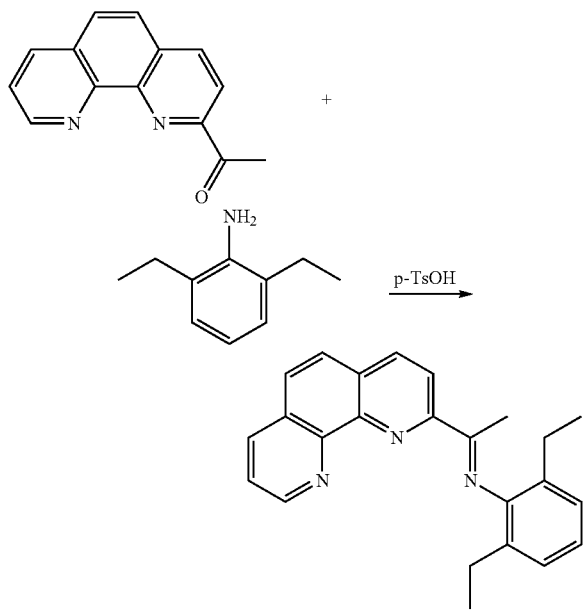

Into a 100 ml two-necked flask equipped with a water separator, 0.47 g of 2-acetyl-1,10-phenanthroline (2.12 mmol) obtained in step A, 0.95 g of 2,6-diethyl aniline (6.36 mmol) and 35 ml of toluene without water and oxygen are added, wherein the molar ratio of 2-acetyl-1,10-phenanthroline to 2,6-diethyl aniline is 1:3. The water separator is equipped with a condenser tube, wherein 0.01 g of p-toluenesulfonic acid is added, and the reflux is carried out at 110° C. for 6 h. After the removal of the solvent at reduced pressure, a mixed solution of ethyl acetate and petroleum ether with a volume ratio of 1:4 is used as an eluent, and a luminous yellow product with a weight of 0.61 g and a yield of 81% is obtained after silica gel column chromatography. The product is identified as 2-acetyl-1,10-phenanthroline (2,6-diethylanil) ligand by Nuclear Magnetic Resonance, Mass Spectrometry and Elemental analysis.

Mass Spectrometry MS-EI: 353.

Nuclear Magnetic Resonance analysis: $^1$H NMR (300 MHz, CDCl$_3$): δ9.25(dd, J=3.0 Hz, 1H); 8.80(d, J=8.3 Hz, 1H); 8.35(d, J=8.3 Hz, 1H); 8.27(dd, J=7.8 Hz, 1H); 7.86(s, 2H); 7.66(m, 1H); 7.15(d, J=7.6 Hz, 2H); 6.96(t, J=7.5 Hz, 1H); 2.58(s, 3H, CH$_3$); 2.43(m, 4H, CH$_2$CH$_3$), 1.16(t, J=7.5 Hz, 6H, CH$_2$CH$_3$).

Element analysis: C$_{24}$H$_{23}$N$_3$ (353.46), theoretical values: C, 81.55; H, 6.56; N, 11.89; measured values: C, 80.88; H, 6.59; N, 11.78.

Step C: Synthesis of 2-acetyl-1,10-phenanthroline (2,6-diethylanil) iron (II) Chloride

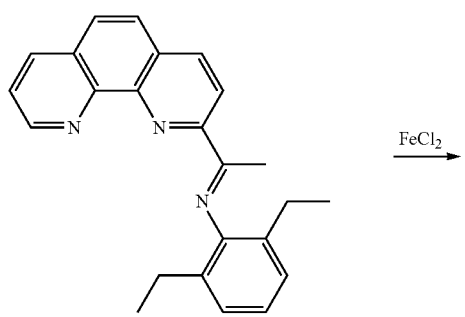

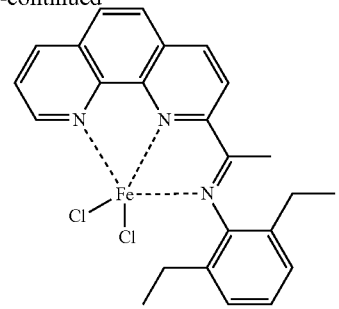

0.16 g of ferrous chloride (1.25 mmol) is dissolved by 20 ml of tetrahydrofuran without water and oxygen in a two-necked flask under nitrogen. 0.48 g of 2-acetyl-1,10-phenanthroline (2,6-diethylanil) ligand (1.36 mmol) obtained in step B is separately dissolved in 20 ml of tetrahydrofuran without water and oxygen. The above two solutions are combined at room temperature under nitrogen, when reaction occurs immediately, and the solution shows grayish black. The solution is stirred over night at room temperature and under nitrogen. The reaction is detected by TLC until 2-acetyl-1,10-phenanthroline (2,6-diethylanil) ligand disappears basically. After suction filtration, anhydrous diethyl ether is used for washing, and a silver-gray solid is obtained after vacuum drying. The solid is confirmed as 2-acetyl-1,10-phenanthroline (2,6-diethylanil) iron (II) chloride, whose element analysis results are shown as follows:

Element analysis: C$_{24}$H$_{23}$Cl$_2$FeN$_3$ (480.22), theoretical values: C, 60.09; H, 4.90; N, 8.76; measured values: C, 60.03; H, 4.83; N, 8.75.

2. Ethylene Oligomerization

Toluene, 0.53 ml of toluene solution (0.74 mol/l) of methyl aluminoxane and 8 ml of toluene solution of the main catalyst 2-acetyl-1,10-phenanthroline (2,6-diethylanil) iron (II) chloride (2.0 μmol) are added into a 300 ml stainless autoclave, wherein the total volume of reactants is 100 ml, and the molar ratio of Al to Fe is 196. When the polymerization temperature reaches 40° C., ethylene is fed into the reactor, the ethylene pressure is kept at 1 MPa and the reaction is carried out for 30 min under stirring. Then a small amount of the mixture is taken out by a syringe, and after being neutralized by 5% dilute hydrochloric acid, the product therein is analyzed by GC. The result shows that the oligomerization activity is $2.02 \times 10^6$ g·mol$^{-1}$(Fe)·h$^{-1}$, and the oligomer contents are respectively as follow, C$_4$: 12.0%, C$_6$~C$_{10}$: 64.7%, C$_6$-C$_{18}$: 87.0% (wherein 98.0% liner alpha olefins are contained), C$_{20}$-C$_{28}$: 1.0%, and the K value is 0.57. The residual reaction mixtures are neutralized by ethanol solution which is acidified by 5% dilute hydrochloric acid, and no polymers are obtained.

Example 51

1. Synthesis of the Catalyst 2-n-propionyl-1,10-phenanthroline(2,6-diethylanil) iron (II) Chloride Complex Step A: Synthesis of 2-n-propionyl-1,10-phenanthroline

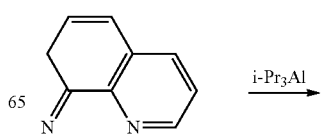

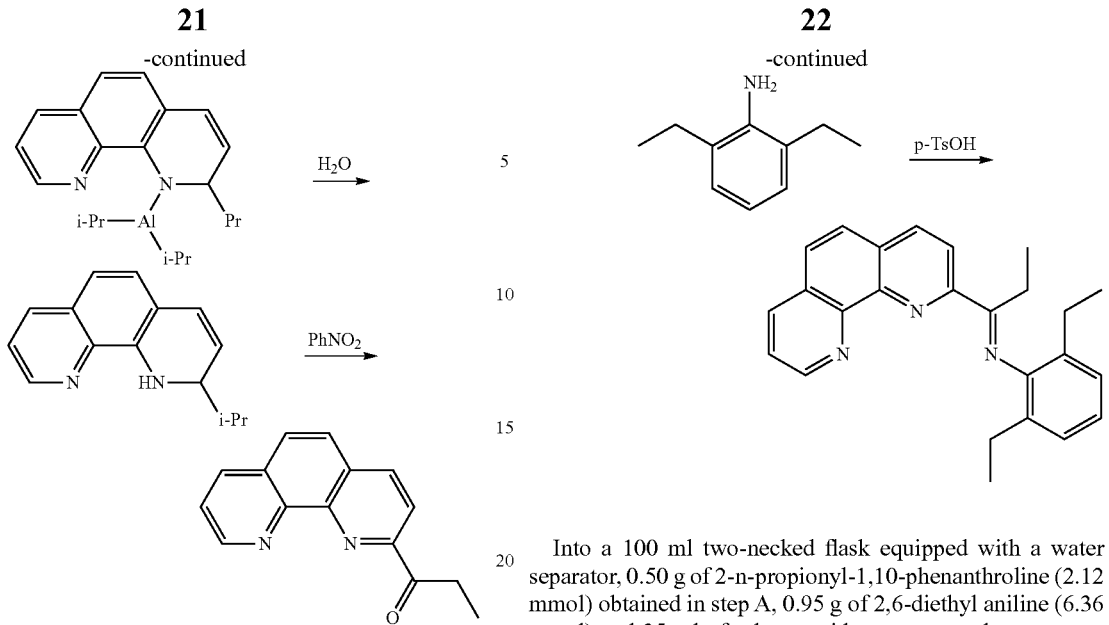

5.1 g of 1,10-phenanthroline (28.3 mmol) is fed into a 250 ml three-necked flask, and dissolved in 100 ml of toluene under nitrogen and magnetic stirring. 13.5 ml of trin-propyl aluminum (d=0.82 g/ml, 70.9 mmol) is added slowly and dropwise into the three-necked flask under stirring at −60° C. within about 15 min, the stirring is continued for 18 h at −60° C., the temperature is raised to about 30° C., and the stirring continued for 10 h. Then the reaction mixture is cooled to about −30° C., and 50 ml of distilled water is added into it slowly, the temperature is raised to 30° C. and the mixture is stirred for 10 h. Then the mixture is separated, wherein the organic phase is taken out, and the inorganic phase is extracted by dichloromethane for 3 times, the amount of dichloromethane being 20 ml each time, and the organic phases are combined. The solvent is removed in the combined organic phase under reduced pressure, and 50 ml nitrobenzene (1.205 g/ml) is added, which is then refluxed at 210° C. for about 50 h. After filtration, nitrobenzene is removed at a pressure lower than 10 mmHg, and a black viscous liquid substance is obtained. The mixed solution of ethyl acetate and petroleum ether with a volume ratio of 1:2 is used as an eluent to make silica gel column chromatography on the black viscous liquid substance, and a brown product is obtained with a weight of 2.0 g and a yield of 30%. The product is identified as 2-n-propionyl-1,10-phenanthroline by Nuclear Magnetic Resonance and Mass Spectrometry.

Mass Spectrometry MS-EI: 236.

Nuclear Magnetic Resonance analysis, $^1$H NMR(400 MHz, CDCl$_3$): δ9.26(dd, J=1.72, 1H); 8.33(s, 2H); 8.27(dd, J=1.68, 1H); 7.86(d, J=8.8, 1H); 7.80(d, J=8.8, 1H); 7.68(dd, J=5.28, 1H); 3.67(m, J=7.24, 2H); 1.10(t, J=7.4, 3H).

Step B: Synthesis of 2-n-propionyl-1,10-phenanthroline (2,6-diethylanil) Ligand

Into a 100 ml two-necked flask equipped with a water separator, 0.50 g of 2-n-propionyl-1,10-phenanthroline (2.12 mmol) obtained in step A, 0.95 g of 2,6-diethyl aniline (6.36 mmol) and 35 ml of toluene without water and oxygen are added, wherein the molar ratio of 2-n-propionyl-1,10-phenanthroline to 2,6-diethyl aniline is 1:3. The water separator is equipped with a condenser tube, wherein 0.01 g of p-toluenesulfonic acid is added, and a reflux is carried out at 110° C. for 6 h. After the removal of the solvent at a reduced temperature, a mixed solution of ethyl acetate and petroleum ether with a volume ratio of 1:4 is used as an eluent, and a luminous yellow product with a weight of 0.63 g and a yield of 81% is obtained after silica gel column chromatography. The product is identified as 2-n-propionyl-1,10-phenanthroline (2,6-diethylanil) ligand by Nuclear Magnetic Resonance, Mass Spectrometry and Elemental analysis.

Mass Spectrometry MS-EI: 367.

Nuclear Magnetic Resonance analysis, $^1$H NMR(400 MHz, CDCl$_3$): δ9.25(dd, J=2.96, 1H); 8.66(d, J=8.36, 1H); 8.33 (d, J=8.36, 1H); 8.28(dd, J=7.84, 1H); 7.85(dd, J=9.02, 2H); 7.65(dd, J=4.36, 1H); 7.15(d, J=7.52, 2H); 7.06(t, J=7.04, 1H); 3.01(t, J=7.84, —CNCH$_2$CH$_3$,2H); 2.40(m, J=7.52, phCH$_2$CH$_3$,2H); 1.20(t, J=7.30, phCH$_2$CH$_3$, 6H); 0.90(t, J=7.32, CH$_3$CH$_2$CN, 3H).

Element analysis: C$_{25}$H$_{25}$N$_3$ (367.49), theoretical values: C, 81.71; H, 6.86; N, 11.43; measured values: C, 81.66; H, 6.87; N, 11.47.

Step C: Synthesis of 2-n-propionyl-1,10-phenanthroline (2,6-diethylanil) iron (II) Chloride

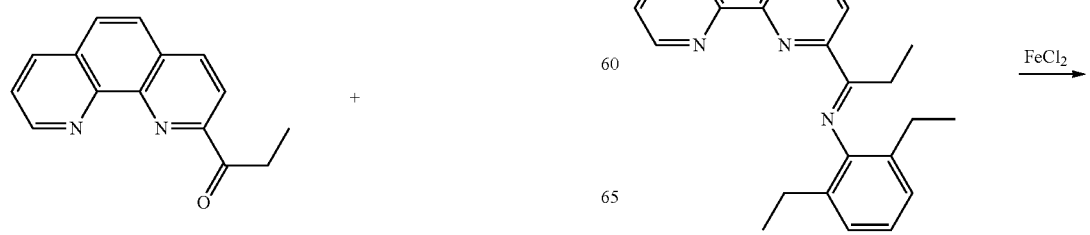

0.16 g of ferrous chloride (1.25 mmol) is dissolved by 20 ml of tetrahydrofuran without water and oxygen in a two-necked flask under nitrogen. 0.50 g of 2-n-propionyl-1,10-phenanthroline (2,6-diethylanil) ligand (1.36 mmol) obtained in step B is separately dissolved in 20 ml of tetrahydrofuran without water and oxygen. The above two solutions are combined at room temperature under nitrogen, when reaction occurs immediately, and the solution shows grayish black. The solution is stirred overnight at room temperature and under nitrogen. The reaction is detected by TLC until 2-n-propionyl-1,10-phenanthroline (2,6-diethylanil) ligand disappears basically. After suction filtration, anhydrous diethyl ether is used for washing, and a silver-gray solid is obtained after vacuum drying. The solid is confirmed as 2-n-propionyl-1,10-phenanthroline (2,6-diethylanil) iron (II) chloride, whose element analysis results are shown as follows.

Element analysis: $C_{25}H_{25}Cl_2FeN_3$ (494.24), theoretical values: C, 60.75; H, 5.10; N, 8.50; measured values: C, 60.71; H, 5.00; N, 8.53.

2. Ethylene Oligomerization

Toluene, 2.66 ml of toluene solution (1.5 mol/l) of methyl aluminoxane (4.0 mmol) and 8 ml of toluene solution of the main catalyst 2-n-propionyl-1,10-phenanthroline (2,6-diethylanil) iron (II) chloride (2.0 μmol) are added into a 300 ml stainless autoclave, wherein the total volume of the reactants is 100 ml, and the molar ratio of Al to Fe is 2000. When the polymerization temperature reaches 40° C., ethylene is fed into the reactor, the ethylene pressure is kept at 1 MPa and the reaction is carried out for 30 min under stirring. Then a small amount of the mixture is taken out by a syringe, and after being neutralized by 5% dilute hydrochloric acid, it is analyzed by GC. The result shows that the oligomerization activity is $1.36 \times 10^7$ $g \cdot mol^{-1}(Fe) \cdot h^{-1}$, and the oligomer contents are respectively as follow, $C_4$: 23.30%, $C_6 \sim C_{10}$: 60.33%, $C_6$-$C_{18}$: 75.12% (wherein 96.1% liner alpha olefins are contained), $C_{20}$-$C_{28}$: 1.58%, and the K value is 0.63. The residual reaction mixtures are neutralized by ethanol solution which is acidified by 5% dilute hydrochloric acid, and small amount of white waxy polymers are obtained. The polymerization activity is $5.32 \times 10^4$ $g \cdot mol^{-1} \cdot h^{-1}$.

Example 52

1. Synthesis of the catalyst 2-iso-butyryl-1,10-phenanthroline (2,6-diethylanil) iron (II) Chloride Complex Step A: Synthesis of 2-iso-butyryl-1,10-phenanthroline

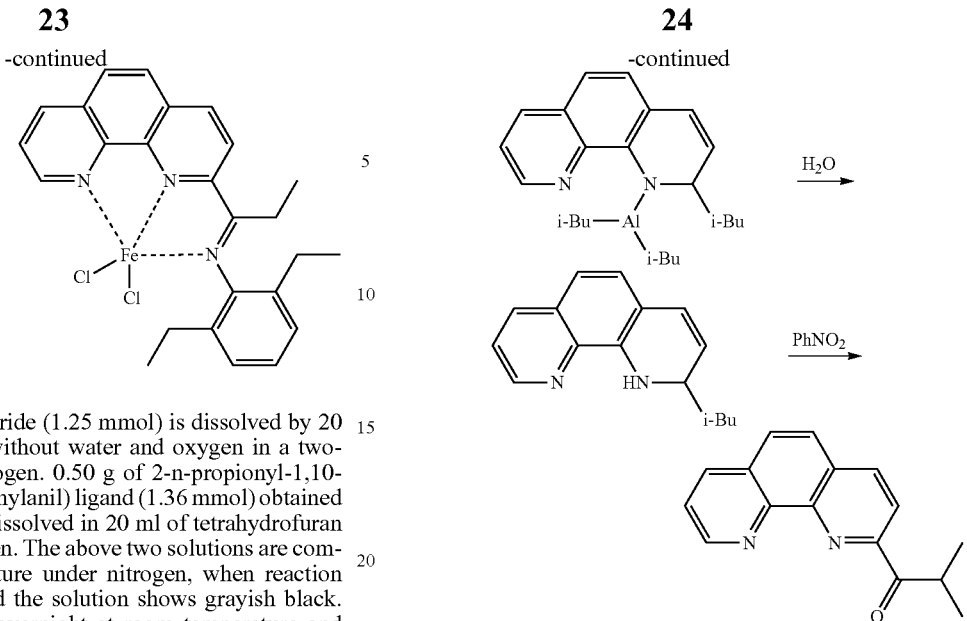

5.1 g of 1,10-phenanthroline (28.3 mmol) is added into a 250 ml three-necked flask, and is dissolved in 100 ml of toluene under nitrogen and magnetic stirring. 13.7 ml of triiso-butyl aluminum (d=0.82 g/ml, 56.6 mmol) is added slowly and dropwise into the three-necked flask under stirring at −60° C. within about 15 min, the stirring is continued for 18 h at −60° C., the temperature is raised to about 30° C., and the stirring is continued for 10 h. The reaction mixture is cooled to about −30° C., and 50 ml of distilled water is added into it slowly, after which the temperature is raised to 30° C. and the stirring is continued for 10 h. Then the mixture is separated, wherein the organic phase is taken out, and the inorganic phase is extracted by dichloromethane for 3 times, the amount of dichloromethane being 20 ml each time, and the organic phases are combined. The solvent in the combined organic phase is removed under reduced pressure, and 50 ml nitrobenzene (1.205 g/ml) is added, which is then refluxed at 210° C. for about 50 h. After filtration, nitrobenzene is removed at a pressure lower than 10 mmHg, and a black viscous liquid substance is obtained. The mixed solution of ethyl acetate and petroleum ether with a volume ratio of 1:2 as an eluent is used to make silica gel column chromatography on the black viscous liquid substance, and a brown product is obtained with a weight of 2.1 g and a yield of 30%. The product is identified as 2-iso-butyryl-1,10-phenanthroline by Nuclear Magnetic Resonance and Mass Spectrometry.

Mass Spectrometry MS-EI: 250.

Nuclear Magnetic Resonance analysis, $^1H$ NMR(400 MHz, $CDCl_3$): δ9.26(dd, J=1.72, 1H); 8.33(s, 2H); 8.27(dd, J=1.68, 1H); 7.86(d, J=8.8, 1H); 7.80 (d, J=8.8, 1H); 7.68(dd, J=5.28, 1H); 3.47(m, J=7.24, 1H); 1.10(t, J=7.4, 6H).

Step B: Synthesis of 2-iso-butyryl-1,10-phenanthroline (2,6-diethylanil) Ligand

-continued

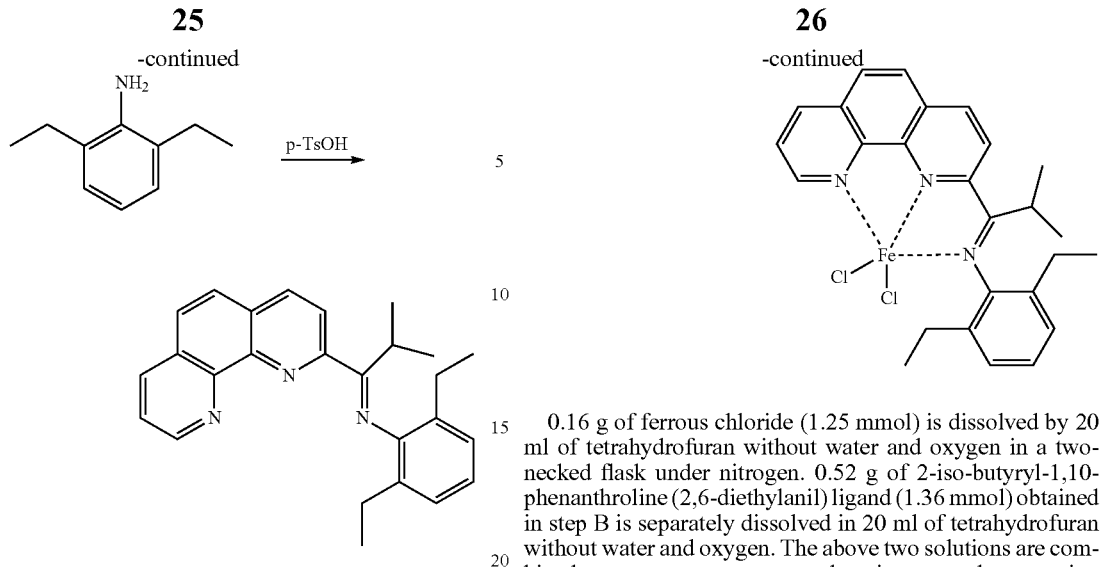

Into a 100 ml two-necked flask equipped with a water separator, 0.53 g of 2-iso-butyryl-1,10-phenanthroline (2.12 mmol) obtained in step A, 0.95 g of 2,6-diethyl aniline (6.36 mmol) and 35 ml of toluene without water and oxygen are added, wherein the molar ratio of 2-iso-butyryl-1,10-phenanthroline to 2,6-diethyl aniline is 1:3. The water separator is equipped with a condenser tube, wherein 0.01 g of p-toluenesulfonic acid is added, and reflux is carried out at 110° C. for 6 h. After the removal of the solvent under reduced pressure, a mixed solution of ethyl acetate and petroleum ether with a volume ratio of 1:4 is used as an eluent, and a luminous yellow product with a weight of 0.65 g and a yield of 81% is obtained after silica gel column chromatography. The product is identified as 2-iso-butyryl-1,10-phenanthroline (2,6-diethylanil) ligand by Nuclear Magnetic Resonance, Mass Spectrometry and Elemental analysis.

Mass Spectrometry MS-EI: 381.

Nuclear Magnetic Resonance analysis, $^1$H NMR(400 MHz, CDCl$_3$): δ9.25(dd, J=2.96, 1H); 8.66 (d, J=8.36, 1H); 8.33(d, J=8.36, 1H); 8.28(dd, J=7.84, 1H); 7.85(dd, J=9.02, 2H); 7.65(dd, J=4.36, 1H); 7.15(d, J=7.52, 2H); 7.06(t, J=7.04, 1H); 3.01(m, J=7.84, —CNCH(CH$_3$)$_2$, 1H); 2.40(m, J=7.52, phCH$_2$CH$_3$,4H); 1.58(d, J=7.44, —CNCH(CH$_3$)$_2$, 6H); 1.20(t, J=7.30, phCH$_2$CH$_3$, 6H).

Element analysis: C$_{26}$H$_{27}$N$_3$ (381.51), theoretical values: C, 81.85; H, 7.13; N, 11.01; measured values: C, 81.36; H, 7.23; N, 10.55.

Step C: Synthesis of 2-iso-butyryl-1,10-phenanthroline (2,6-diethylanil) iron (II) Chloride

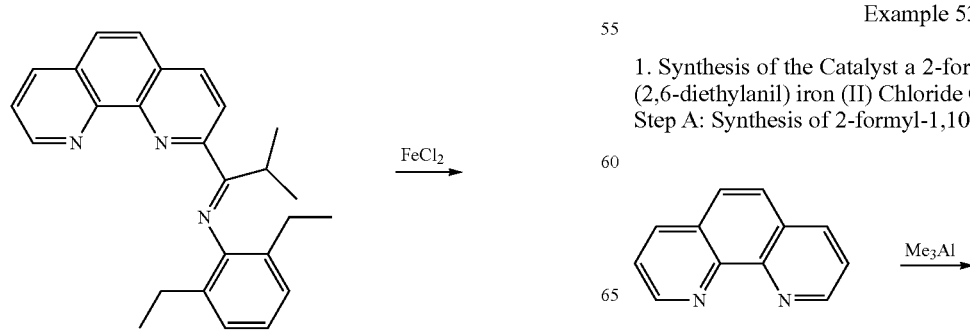

0.16 g of ferrous chloride (1.25 mmol) is dissolved by 20 ml of tetrahydrofuran without water and oxygen in a two-necked flask under nitrogen. 0.52 g of 2-iso-butyryl-1,10-phenanthroline (2,6-diethylanil) ligand (1.36 mmol) obtained in step B is separately dissolved in 20 ml of tetrahydrofuran without water and oxygen. The above two solutions are combined at room temperature under nitrogen, when reaction occurs immediately, and the solution shows grayish black. The solution is stirred overnight at room temperature under nitrogen. The reaction is detected by TLC until 2-iso-butyryl-1,10-phenanthroline (2,6-diethylanil) ligand disappears basically. After suction filtration, anhydrous diethyl ether is used for washing, and a silver-gray solid is obtained after vacuum drying. The solid is confirmed as 2-iso-butyryl-1,10-phenanthroline (2,6-diethylanil) iron (II) chloride. The results of element analysis are as follows.

Element analysis, C$_{26}$H$_{27}$Cl$_2$FeN$_3$ (508.26), theoretical values: C, 61.44; H, 5.35; N, 8.27; measured values: C, 61.79; H, 5.60; N, 8.13.

2. Ethylene Oligomerization

Toluene, 1.33 ml of the toluene solution (1.5 mol/l) of methyl aluminoxane (2.0 mmol) and 8 ml of the toluene solution (2.0 mol) of the main catalyst 2-iso-butyryl-1,10-phenanthroline (2,6-diethylanil) iron (II) chloride are added into a 300 ml stainless autoclave, wherein the total volume of the reactants is 100 ml, and the molar ratio of Al to Fe is 1000. When the polymerization temperature reaches 40° C., ethylene is fed into the reactor, the ethylene pressure is kept at lMPa and the reaction is carried out for 30 min under stirring. Then a small amount of the mixture is taken out by a syringe, and after being neutralized by 5% dilute hydrochloric acid, it is analyzed by GC. The result shows that the oligomerization activity is 2.51×10$^7$ g·mol$^{-1}$(Fe)·h$^{-1}$, and the oligomer contents are respectively as follow: C$_4$: 24.50%, C$_6$~C$_{10}$: 55.63%, C$_6$-C$_{18}$: 71.42% (wherein 97.0% liner alpha olefins are contained), C$_{20}$-C$_{28}$: 4.08%, and the K value is 0.63. The residual reaction mixtures are neutralized by ethanol solution which is acidified by 5% dilute hydrochloric acid, and white waxy polymers are obtained, wherein the polymerization activity is 3.98×10$^4$ g·mol$^{-1}$·h$^1$.

Example 53

1. Synthesis of the Catalyst a 2-formyl-1,10-phenanthroline (2,6-diethylanil) iron (II) Chloride Complex
Step A: Synthesis of 2-formyl-1,10-phenanthroline

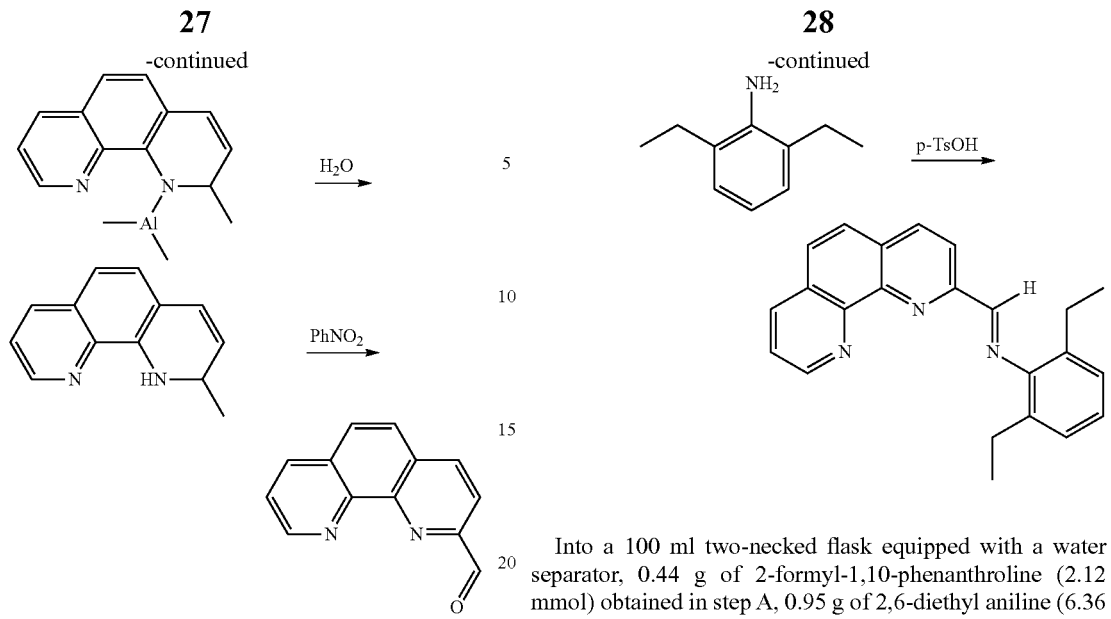

5.1 g of 1,10-phenanthroline (28.3 mmol) is fed into a 250 ml three-necked flask, and is dissolved in 100 ml of toluene under nitrogen and magnetic stirring. 3 ml of trimethyl aluminum (d=0.75 g/ml, 31.3 mmol) is added slowly and dropwise into the three-necked flask under stirring at −60° C. within about 15 min. The stirring is continued for 18 h at −60° C., the temperature is raised to about 30° C., and the stirring is continued for 10 h. Then the reaction mixture is cooled to about −30° C., and 50 ml of distilled water is added into the mixture slowly, after which the temperature is raised to 30° C. and the stirring is continued for 10 h. Then the mixture is separated, wherein the organic phase is taken out, and the inorganic phase is extracted by dichloromethane for 3 times, the amount of dichloromethane being 20 ml each time, and the organic phases are combined. The solvent in the combined organic phase is removed under reduced pressure, and 50 ml of nitrobenzene (1.205 g/ml) is added, which is then refluxed at 210° C. for about 48 h. After filtration, nitrobenzene is removed at a pressure lower than 10 mmHg, and a black viscous liquid substance is obtained. The mixed solution of ethyl acetate and petroleum ether with a volume ratio of 1:2 is used as an eluent to make silica gel column chromatography on the black viscous liquid substance, and a brown product is obtained with a weight of 1.8 g and a yield of 30%. The product is identified as 2-formyl-1,10-phenanthroline by Nuclear Magnetic Resonance and Mass Spectrometry.

Mass Spectrometry MS-EI: 208.

Nuclear Magnetic Resonance analysis, $^1$H NMR (400 MHz, CDCl$_3$): δ9.26 (d, J=3.9 HZ, 1H); 9.16(s, 1H); 8.37(s, 2H); 8.29(d, J=8.1 HZ, 1H); 8.7(dd, J=8.7 HZ, 2H); 7.69(dd, J=7.8 HZ, 1H).

Step B: Synthesis of 2-formyl-1,10-phenanthroline (2,6-diethylanil) Ligand

Into a 100 ml two-necked flask equipped with a water separator, 0.44 g of 2-formyl-1,10-phenanthroline (2.12 mmol) obtained in step A, 0.95 g of 2,6-diethyl aniline (6.36 mmol) and 35 ml of toluene without water and oxygen are added, wherein the molar ratio of 2-formyl-1,10-phenanthroline to 2,6-diethyl aniline is 1:3. The water separator is equipped with a condenser tube, wherein 0.01 g of p-toluenesulfonic acid is added, and refluxed at 110° C. for 6 h. After the removal of solvent at reduced pressure, a mixed solution of ethyl acetate and petroleum ether with a volume ratio of 1:4 is used as an eluent, and a luminous yellow product with a weight of 0.58 g and a yield of 81% is obtained after silica gel column chromatography. The product is identified as 2-formyl-1,10-phenanthroline (2,6-diethylanil) ligand by Nuclear Magnetic Resonance, Mass Spectrometry and Elemental analysis.

Mass Spectrometry MS-EI: 339.

Nuclear Magnetic Resonance analysis, $^1$H NMR(400 MHz, CDCl$_3$): δ9.25(dd, J=3.0 Hz, 1H); 9.16(s, 1H); 8.80(d, J=8.3 Hz, 1H); 8.35(d, J=8.3 Hz, 1H); 8.27(dd, J=7.8 Hz, 1H); 7.86 (s, 2H); 7.66(m, 1H); 7.15(d, J=7.6 Hz, 2H); 6.96(t, J=7.5 Hz, 1H); 2.43(m, 4H, CH$_2$CH$_3$); 1.16(t, J=7.5 Hz, 6H, CH$_2$CH$_3$).

Element analysis: C$_{24}$H$_{23}$N$_3$ (353.46), theoretical values: C, 81.38; H, 6.24; N, 12.38; measured values: C, 81.48; H, 6.59; N, 12.39.

Step C: Synthesis of 2-formyl-1,10-phenanthroline (2,6-diethylanil) iron (II) Chloride

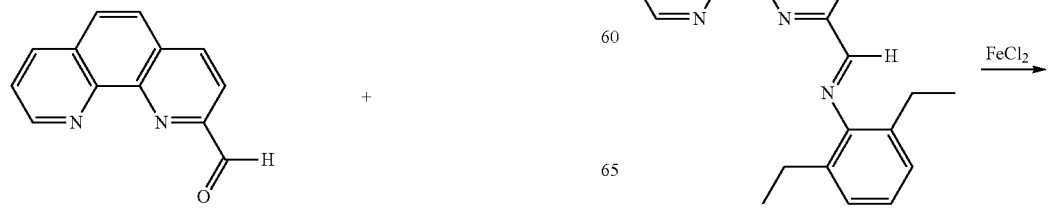

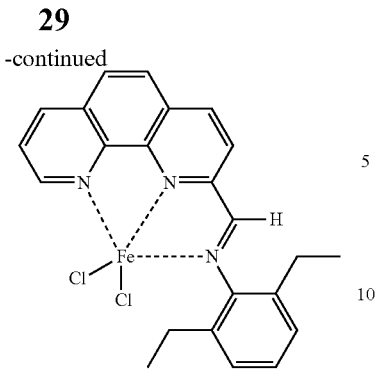

0.16 g of ferrous chloride (1.25 mmol) is dissolved by 20 ml of tetrahydrofuran without water and oxygen in a two-necked flask under nitrogen. 0.46 g of 2-formyl-1,10-phenanthroline (2,6-diethylanil) ligand (1.36 mmol) obtained in step B is separately dissolved in 20 ml of tetrahydrofuran without water and oxygen. The above two solutions are combined at room temperature under nitrogen, when reaction occurs immediately, and the solution shows grayish black. The solution is stirred overnight at room temperature under nitrogen. The reaction is detected by TLC until 2-formyl-1,10-phenanthroline (2,6-diethylanil) ligand disappears basically. After suction filtration, anhydrous diethyl ether is used for washing, and a silver-gray solid is obtained with a yield of 97% after vacuum drying. The solid is confirmed as 2-formyl-1,10-phenanthroline (2,6-diethylanil) iron (II) chloride, whose element analysis results are shown as follows.

Element analysis: $C_{24}H_{23}Cl_2FeN_3$ (508.26), theoretical values: C, 59.26; H, 4.54; N, 9.01; measured values: C, 59.38; H, 4.83; N, 8.92.

2. Ethylene Oligomerization

Toluene, 1.33 ml of the toluene solution (1.5 mol/l) of methyl aluminoxane (2.0 mmol) and 8 ml of the toluene solution of the main catalyst 2-formyl-1,10-phenanthroline (2,6-diethylanil) iron (II) chloride are added into a 300 ml stainless autoclave, wherein the total volume of the reactants is 100 ml, and the molar ratio of Al to Fe is 1000. When the polymerization temperature reaches 40° C., ethylene is fed into the reactor, the ethylene pressure is kept at 1 MPa and the reaction is carried out for 30 min under stirring. Then a small amount of the mixture is taken out by a syringe, and after being neutralized by 5% dilute hydrochloric acid, it is analyzed by GC. The result shows that the oligomerization activity is $1.51 \times 10^6$ $g \cdot mol^{-1}(Fe) \cdot h^{-1}$, and the oligomer contents are respectively as follow, $C_4$: 28.71%, $C_6$~$C_{10}$: 55.10%, $C_6$-$C_{18}$: 69.69% (wherein 98.5% liner alpha olefins are contained), $C_{20}$-$C_{28}$: 1.60%, and the K value is 0.59. The residual reaction mixtures are neutralized by ethanol solution which is acidified by 5% dilute hydrochloric acid, and a white waxy polymer is obtained, whose polymerization activity is $3.85 \times 10^3$ $g \cdot mol^{-1} \cdot h^{-1}$.

Example 54

1. Synthesis of the Catalyst a 2-benzoyl-1,10-phenanthroline (2,6-diethylanil) iron (II) Chloride Complex Step A: Synthesis of 2-benzoyl-1,10-phenanthroline

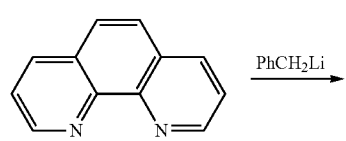

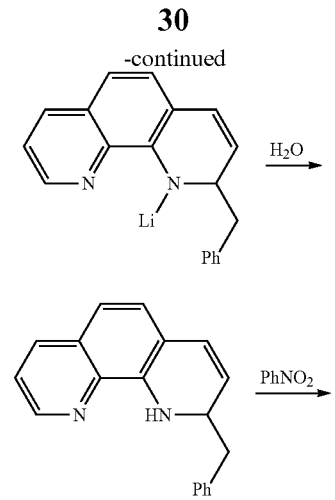

5.1 g of 1,10-phenanthroline is fed (28.3 mmol) into a 250 ml three-necked flask, and is dissolved in 100 ml of toluene under nitrogen and magnetic stirring. 60 ml of the hexane solution (1.2M) of benzyl Li (0.07 mmol) is added slowly and dropwise into the three-necked flask under stirring at −60° C. within about 15 min. The stirring is continued for 18 h at −60° C., the temperature is raised to about 30° C., and the stirring is continued for 10 h. Then the reaction mixture is cooled to about −30° C., and 50 ml of distilled water is added into it slowly, after which the temperature is raised to 30° C. and the stirring is continued for 10 h. Then the mixture is separated, wherein the organic phase is taken out, and the inorganic phase is extracted by dichloromethane for 3 times, the amount of dichloromethane being 20 ml each time, and the organic phases are combined. The solvent in the combined organic phase is removed under reduced pressure. Then 50 ml of nitrobenzene (1.205 g/ml) is added, which is then refluxed at 210° C. for about 60 h. After filtration, nitrobenzene is removed at a pressure lower than 10 mmHg, and a black viscous liquid substance is obtained. The mixed solution of ethyl acetate and petroleum ether with a volume ratio of 1:2 is used as an eluent to make silica gel column chromatography on the black viscous liquid substance, and a brown product is obtained with a weight of 2.4 g and a yield of 30%. The product is identified as 2-benzoyl-1,10-phenanthroline by Nuclear Magnetic Resonance and Mass Spectrometry.

Mass Spectrometry MS-EI: 284.

Nuclear Magnetic Resonance analysis, 1H NMR (300 MHz, CDCl3): δ9.18 (dd, J=2.1 Hz, 1H); 8.44(s, 1H); 8.41(s, 1H); 8.39(d, J=3.3 Hz, 1H); 8.27-8.23 (m, 2H); 7.86-7.83(m, 2H); 7.66-7.58(m, 2H); 7.54-7.49(m, 2H). 13C NMR(100 MHz, CDCl3):δ193.2, 154.8, 150.7, 146.3, 144.8, 136.9, 136.1, 135.9, 133.1, 131.8, 129.5, 129.0, 128.4, 128.2, 126.0, 123.1, 122.9.

Element analysis: $C_{19}H_{12}N_2O$ (284.31), theoretical values: C, 80.27; H, 4.25; N, 9.85; measured values: C, 80.24; H, 4.24; N, 9.83.

Step B: Synthesis of 2-benzyl-1,10-phenanthroline (2,6-diethylanil) Ligand

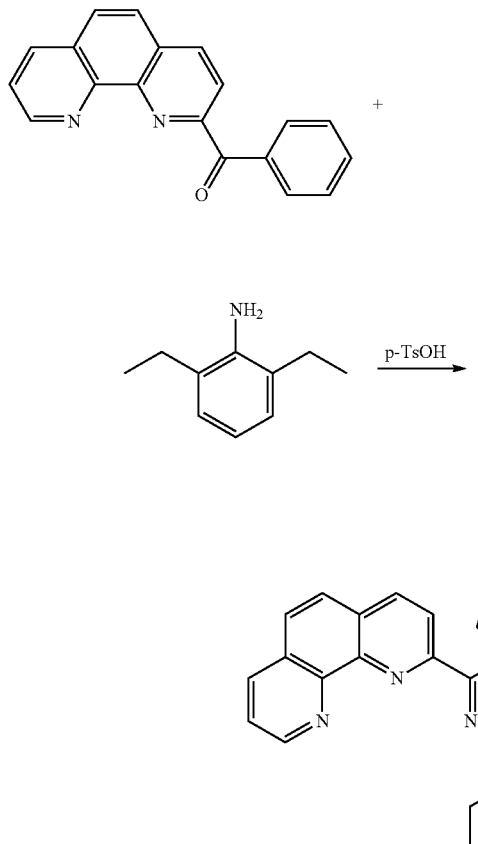

Step C: Synthesis of 2-benzoyl-1,10-phenanthroline (2,6-diethylanil) iron (II) Chloride

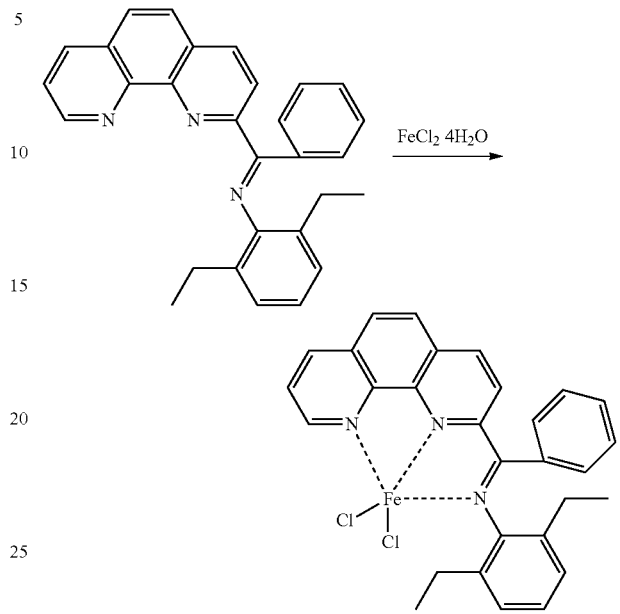

Into a 100 ml two-necked flask equipped with a water separator, 0.47 g of 2-benzoyl-1,10-phenanthroline (1.65 mmol) obtained in step A, 0.74 g of 2,6-diethyl aniline (4.96 mmol) and 35 ml of toluene without water and oxygen are added, wherein the molar ratio of 2-benzoyl-1,10-phenanthroline to 2,6-diethyl aniline is 1:3. The water separator is equipped with a condenser tube, wherein 0.01 g of p-toluenesulfonic acid is added, and refluxed at 110° C. for 6 h.

After the removal of the solvent at reduced pressure, a mixed solution of ethyl acetate and petroleum ether with a volume ratio of 1:4 is used as an eluent, and a luminous yellow product with a weight of 0.55 g and a yield of 81% is obtained after silica gel column chromatography. The product is identified as 2-benzoyl-1,10-phenanthroline (2,6-diethylanil) ligand by Nuclear Magnetic Resonance, Mass Spectrometry and Elemental analysis.

Mass Spectrometry MS-EI: 415.

Nuclear Magnetic Resonance analysis, 1H NMR (400 MHz, CDCl3): δ9.17-6.80(m, 15H); 2.85-2.71(m, 2H); 2.56-2.44(m, 2H); 1.17(t, J=7.5 Hz, 6H). 13C NMR(100 MHz, CDCl3):δ165.1, 155.5, 150.5, 147.7, 146.3, 145.6, 137.9, 136.5, 135.9, 135.7, 131.9, 130.8, 130.1, 129.5, 129.0, 128.3, 127.9, 127.5, 127.3, 126.3, 125.6, 125.1, 123.7, 123.1, 122.0, 24.9, 24.6, 13.5.

Element analysis: $C_{31}H_{29}N_3$ (415.53); theoretical values: C, 83.82; H, 6.06; N, 10.11; measured values: C, 83.56; H, 6.10; N, 9.98.

0.25 g of ferrous chloride tetrahydrate (1.25 mmol) is dissolved by 20 ml of tetrahydrofuran without water and oxygen in a two-necked flask under nitrogen. 0.48 g of 2-benzoyl-1,10-phenanthroline (2,6-diethylanil) ligand (1.36 mmol) obtained in step B is separately dissolved in 20 ml of tetrahydrofuran without water and oxygen. The above two solutions are combined at room temperature under nitrogen, when reaction occurs immediately, and the solution shows grayish black. The solution is stirred overnight at room temperature under nitrogen. The reaction is detected by TLC until 2-benzoyl-1,10-phenanthroline (2,6-diethylanil) ligand disappears basically. After suction filtration, anhydrous diethyl ether is used for washing, and a silver-gray solid is obtained after vacuum drying. The solid is confirmed as 2-benzoyl-1,10-phenanthroline (2,6-diethylanil) iron (II) chloride, whose element analysis result is shown as follows.

Element analysis: $C_{29}H_{25}Cl_2FeN_3$ (542.28), theoretical values: C, 64.23; H, 4.65; N, 7.75; measured values: C, 64.04; H, 4.70; N, 7.66.

The total yield of the target product 2-benzoyl-1,10-phenanthroline (2,6-diethylanil) iron (II) chloride obtained by the above steps is more than 20.0%.

2. Ethylene Oligomerization

Toluene, 0.53 ml of the toluene solution (0.74 mol/l) of methyl aluminoxane (1 mmol) and 8 ml of the toluene solution of the main catalyst 2-benzoyl-1,10-phenanthroline (2,6-diethylanil) iron (II) chloride (2.0 mol) are added into a 300 ml stainless autoclave, wherein the total volume of the reactants is 100 ml, and the molar ratio of Al to Fe is 196. When the polymerization temperature reaches 40° C., ethylene is fed into the reactor, the ethylene pressure is kept at 1MPa and the reaction is carried out for 30 min under stirring. Then a small amount of the mixture is taken out by a syringe, and after being neutralized by 5% dilute hydrochloric acid, it is analyzed by GC. The result shows that the oligomerization activity is $2.02\times10^6$ $g \cdot mol^{-1}(Fe) \cdot h^{-1}$, and the oligomer contents are respectively as follow, $C_4$: 12.0%, $C_6$~$C_{10}$: 64.7%, $C_6$-$C_{18}$: 87.0% (wherein 98.0% liner alpha olefins are contained), $C_{20}$-$C_{28}$: 1.0%, and the K value is 0.57. The residual reaction mixtures are neutralized by ethanol solution which is acidified by 5% dilute hydrochloric acid, and no polymers are obtained.

Example 55

The synthesis of the intermediate 5,6-diethyl-2-acetyl-1,10-phenanthroline

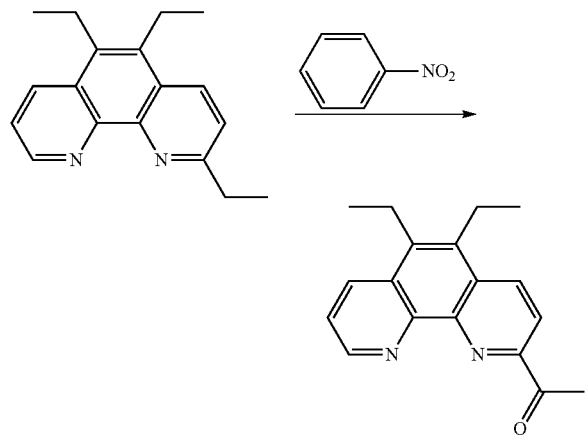

Into a 250 ml three-necked flask, 10.4 g of 2,5,6-triethyl-1,10-phenanthroline (40 mmol) and 60 ml of nitrobenzene (1.205 g/ml) are added and refluxed at 210° C. for about 50 h. After the removal of nitrobenzene at a pressure lower than 10 mmHg, a black viscous liquid substance is obtained. The mixed solution of ethyl acetate and petroleum ether with a volume ratio of 1:2 is used as an eluent to make silica gel column chromatography on the black viscous liquid substance, and brown powders with a weight of 3.3 g and a yield of 30% are obtained. The product is identified as 5,6-diethyl-2-acetyl-1,10-phenanthroline by Mass Spectrometry.

Mass Spectrometry MS-EI: 278.

Example 56

The synthesis of the intermediate 2-acetyl-pyridine

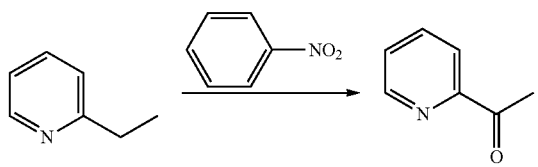

Into a 250 ml three-necked flask, 4.3 g of 2-ethyl-pyridine (40 mmol) and 60 ml of nitrobenzene (1.205 g/ml) are added and refluxed at 210° C. for about 50 h. After the removal of nitrobenzene at a pressure lower than 10 mmHg, a black viscous liquid substance is obtained. The mixed solution of ethyl acetate and petroleum ether with a volume ratio of 1:2 is used as an eluent to make silica gel column chromatography on the black viscous liquid substance, and a colorless liquid with a weight of 1.5 g and a yield of 30% is obtained. The product is identified as 2-acetyl-pyridine by Nuclear Magnetic Resonance and Mass Spectrometry.

Mass Spectrometry MS-EI: 121.

Nuclear Magnetic Resonance analysis, $^1$H NMR (400 MHz, CDCl$_3$): δ8.67 (d, 1H); 8.03 (d, 1H); 7.84 (t, 1H); 7.47 (t, 1H, 2.73 (s, 3H))

Example 57

The synthesis of the intermediate 5-methyl-2-acetyl-pyridine

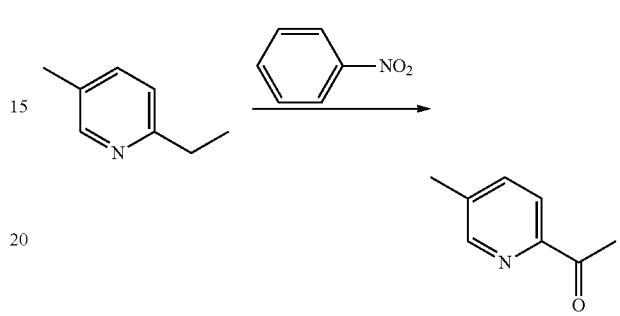

Into a 250 ml three-necked flask, 4.8 g of 5-methyl-2-ethyl-pyridine (40 mmol) and 60 ml of nitrobenzene (1.205 g/ml) are added and refluxed at 110° C. for about 50 h. After the removal of nitrobenzene at a pressure lower than 10 mmHg, a black viscous liquid substance is obtained. The mixed solution of ethyl acetate and petroleum ether with a volume ratio of 1:2 is used as an eluent to make silica gel column chromatography on the black viscous liquid substance, and a colorless liquid with a weight of 1.6 g and a yield of 30% is obtained. The product is identified as 5-methyl-2-acetyl-pyridin by Mass Spectrometry.

Mass Spectrometry MS-EI: 135.

Example 58

The Synthesis of the Intermediate 2,6-diacetyl pyridine

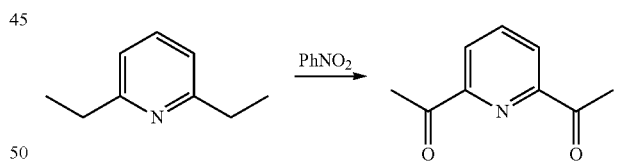

Into a 250 ml three-necked flask, 5.4 g of 2,6-diethyl pyridine (40 mmol) and 60 ml of nitrobenzene (1.205 g/ml) are added and refluxed at 110° C. for about 50 h. After the removal of nitrobenzene at a pressure lower than 10 mmHg, a black viscous liquid substance is obtained. The mixed solution of ethyl acetate and petroleum ether with a volume ratio of 1:2 is used as an eluent to make silica gel column chromatography on the black viscous liquid substance, and a white product with a weight of 2.0 g and a yield of 30% is obtained. The product is identified as 2,6-diacetyl pyridine by Mass Spectrometry.

Mass Spectrometry MS-EI: 163.

Nuclear Magnetic Resonance analysis, $^1$H NMR (400 MHz, CDCl$_3$): δ8.22 (d, 2H); 8.00 (t, 1H); 2.80 (s, 1H).

Example 59

The Synthesis of the Intermediate 2-acetyl quinoline

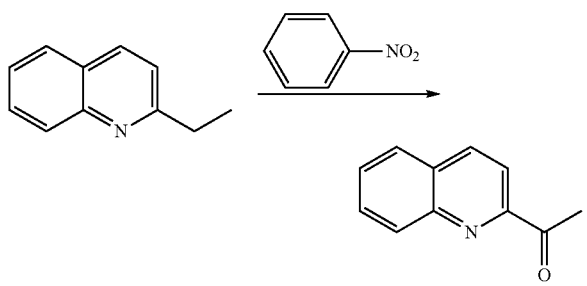

Into a 250 ml three-necked flask, 6.3 g of 2-ethyl quinoline (40 mmol) and 60 ml of nitrobenzene (1.205 g/ml) are added and refluxed at 110° C. for about 50 h. After the removal of nitrobenzene at a pressure lower than 10 mmHg, a black viscous liquid substance is obtained. The mixed solution of ethyl acetate and petroleum ether with a volume ratio of 1:2 is used as an eluent to make silica gel column chromatography on the black viscous liquid substance, and a colorless liquid with a weight of 2.1 g and a yield of 30% is obtained. The product is identified as 2-acetyl quinoline by Mass Spectrometry.

Mass Spectrometry MS-EI: 171.

The invention claimed is:

1. A process for preparing an N ortho acyl substituted nitrogen-containing heterocyclic compound, said process comprising oxidizing an N ortho hydrocarbyl substituted nitrogen-containing heterocyclic compound with a substituted or an unsubstituted nitrobenzene Ph'NO$_2$ as an oxidant to generate said N ortho acyl substituted nitrogen-containing heterocyclic compound, wherein said N ortho hydrocarbyl group is a methyl group or comprises a methylene group directly linked with the nitrogen-containing heterocyclic compound, and the five substituent groups in the benzene ring of said substituted nitrobenzene are independently selected from hydrogen, a $C_1$-$C_6$ alkyl group, a $C_2$-$C_6$ alkenyl or alkynyl group, a halogen, a $C_1$-$C_6$ alkoxy group, and a nitro group,
wherein said N ortho acyl substituted nitrogen-containing heterocyclic compound is a substituted or unsubstituted 2-acyl pyridine as shown in formula B, and said process comprises oxidizing a compound as shown in formula A with the substituted or unsubstituted nitrobenzene as an oxidant to generate the compound as shown in the formula B,

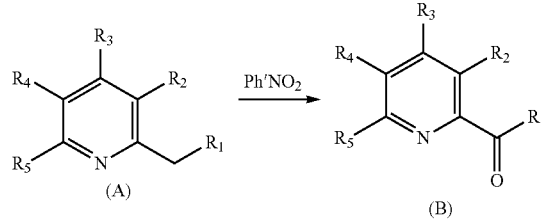

wherein $R_1$ is selected from hydrogen, a $C_1$-$C_6$ alkly group, a $C_2$-$C_6$ alkenyl or alkynyl group, a phenyl group, and a substituted phenyl group, and $R_2$-$R_5$ are independently selected from hydrogen, a $C_1$-$C_6$ alkly group, a $C_2$-$C_6$ alkenyl or alkynyl group, a halogen, a $C_1$-$C_6$ alkoxy group, a nitro group, a phenyl group, and a substituted phenyl group, the five substituent groups in the benzene ring of the substituted phenyl group in $R_1$-$R_5$ being independently selected from a $C_1$-$C_6$ alkenyl or alkynyl group, a halogen, a $C_1$-$C_6$ alkoxy group, and a nitro group.

2. The process according to claim 1, wherein the N ortho acyl substituted nitrogen-containing heterocyclic compound is 2,6-diacetyl pyridine, and said process comprises oxidizing 2,6-diethyl pyridine as shown in formula I' with the substituted or unsubstituted nitrobenzene as an oxidant to generate 2,6-diacetyl pyridine as shown in formula b':

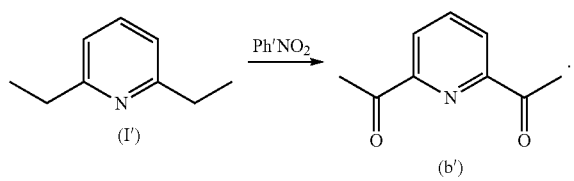

3. A process for preparing an N ortho acyl substituted nitrogen-containing heterocyclic compound, said process comprising oxidizing an N ortho hydrocarbyl substituted nitrogen-containing heterocyclic compound with a substituted or an unsubstituted nitrobenzene Ph'NO$_2$ as an oxidant to generate said N ortho acyl substituted nitrogen-containing heterocyclic compound, wherein said N ortho hydrocarbyl group is a methyl group or comprises a methylene group directly linked with the nitrogen-containing heterocyclic compound, and the five substituent groups in the benzene ring of said substituted nitrobenzene are independently selected from hydrogen, a $C_1$-$C_6$ alkyl group, a $C_2$-$C_6$ alkenyl or alkynyl group, a halogen, a $C_1$-$C_6$ alkoxy group, and a nitro group, wherein the N ortho acyl substituted nitrogen-containing heterocyclic compound is a compound as shown in formula B", and said process comprises oxidizing a compound as shown in formula A" with the substituted or unsubstituted nitrobenzene as an oxidant to generate the compound as shown in formula B",

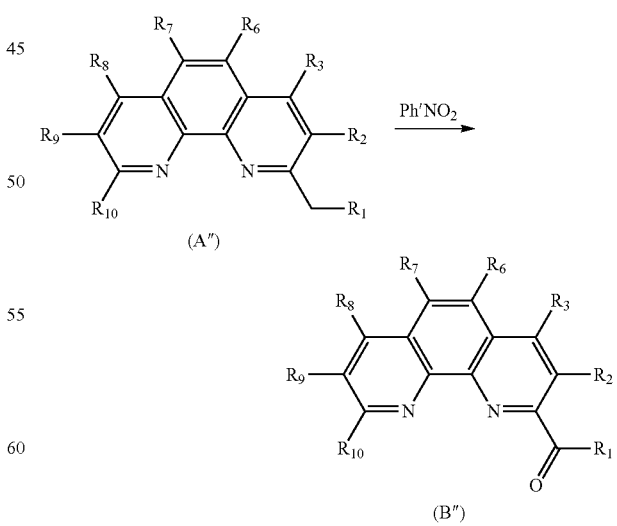

wherein $R_1$ is selected from hydrogen, a $C_1$-$C_6$ alkyl group, a $C_2$-$C_6$ an alkenyl or alkynyl group, a phenyl group, and a substituted phenyl group, and $R_2$-$R_3$ and $R_6$-$R_{10}$ are independently selected from hydrogen, a $C_1$-$C_6$ alkyl group, a $C_2$-$C_6$ alkenyl or alkynyl group, a halogen, a $C_1$-$C_6$ alkoxy group, a nitro group, a phenyl group, and a substituted phenyl group, the five substituent groups in the benzene ring of the substituted phenyl group in $R_1$-$R_{10}$ being independently selected from a $C_1$-$C_6$ alkyl group, a $C_2$-$C_6$ alkenyl or alkynyl group, a halogen, a $C_1$-$C_6$ alkoxy group, and a nitro group.

4. The process according to claim 3, wherein the N ortho acyl substituted nitrogen-containing heterocyclic compound is 2-acyl-1,10-phenanthroline, and said process comprises oxidizing a compound as shown in formula I with the substituted or unsubstituted nitrobenzene as an oxidant to generate 2-acyl-1,10-phenanthroline as shown in formula b,

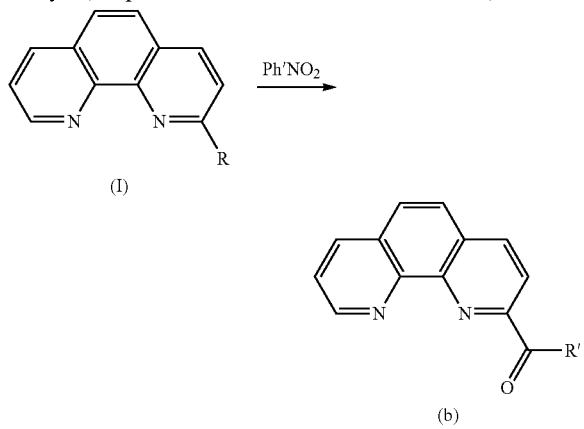

wherein R is a $C_1$-$C_6$ alkyl group, a benzyl group, or a substituted benzyl group, R' is hydrogen or an alkyl group less than R by a $CH_2$, or a substituted phenyl group or an unsubstituted phenyl group, and when R is a substituted benzyl group, the five substituent groups in the benzene ring thereof are independently selected from a $C_1$-$C_6$ alkyl group, a $C_2$-$C_6$ alkenyl or alkynyl group, a halogen, a $C_1$-$C_6$ alkoxy group, and a nitro group.

5. The process according to claim 4, wherein the oxidation reaction is carried out at a temperature ranging from 200 to 220° C. under reflux, and the oxidation reaction time ranges from 10 to 100h.

6. The process according to claim 4, wherein the molar ratio of the compound as shown in formula I to the substituted or unsubstituted nitrobenzene ranges from 1:0.5 to 1:30.

7. The process according to claim 4, wherein said compound as shown in formula I is prepared by the following steps: reacting 1,10-phenanthroline as shown in formula a with a trialkyl aluminum, or a halogenated alkylaluminum $R_nAlX_m$, or a substituted or unsubstituted benzyl lithium Ph'$CH_2$Li, followed by hydrolysis to obtain the compound as shown in formula I,

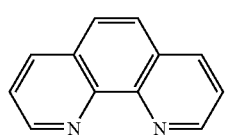

and in the halogenated alkylaluminum $R_nAlX_m$, R can be the same or different $C_1$-$C_6$ alkyl groups, X is a halogen, $1 \leq n \leq 3$, $0 \leq m \leq 2$, and m+n=3.

8. The process according to claim 7, wherein the hydrolysis is carried out in water or alcohol.

9. The process according to claim 7, wherein the molar ratio of said 1,10-phenanthroline to $R_nAlX_m$, or Ph'$CH_2$Li ranges from 1:0.5 to 1:4.5, the reaction temperature of said 1,10-phenanthroline with $R_nAlX_m$, or Ph'$CH_2$Li ranges from −60 to −80° C., and the hydrolysis temperature ranges from −60 to −0° C.

10. The process according to claim 7, wherein the reaction temperature of said 1,10-phenanthroline with $R_nAlX_m$, or Ph'$CH_2$Li ranges from −60 to −70° C., which after a period of reaction is raised to 20 to 40° C., at which the reaction is continued.

11. The process according to claim 1, wherein $R_1$ is selected from hydrogen, a methyl group, an ethyl group, a propyl group, a butyl group, a phenyl group, and the substituted phenyl group, and wherein $R_2$-$R_5$ are independently selected from hydrogen, a methyl group, an ethyl group, a propyl group, a butyl group, a vinyl group, a propenyl group, a butenyl group, an ethynyl group, a propynyl group, a butynyl group, fluorine, chlorine, bromine, a methoxy group, an ethoxy group, a propoxy group, a nitro group, a phenyl group, and the substituted phenyl group.

12. The process according to claim 3, wherein $R_1$ is selected from hydrogen, a methyl group, an ethyl group, a propyl group, a butyl group, a phenyl group, and the substituted phenyl group, and wherein $R_2$-$R_3$ and $R_6$-$R_{10}$ are independently selected from hydrogen, a methyl group, an ethyl group, a propyl group, a butyl group, a vinyl group, a propenyl group, a butenyl group, an ethynyl group, a propynyl group, a butynyl group, fluorine, chlorine, bromine, a methoxy group, an ethoxy group, a propoxy group, a nitro group, a phenyl group, and the substituted phenyl group.

13. The process according to claim 4, wherein R in the compound as shown in formula I is a methyl, an ethyl, a propyl, a butyl, or a benzyl group.

14. The process according to claim 5, wherein the oxidation reaction time ranges from 24 to 60h.

15. The process according to claim 6, wherein the molar ratio of the compound as shown in formula I to the substituted or unsubstituted nitrobenzene ranges from 1:5 to 1:20.

16. The process according to claim 7, wherein the halogenated alkyluminuni $R_nAlX_m$, is at least one compound selected from trimethyl aluminum, triethyl aluminum, trinpropyl aluminum, trin-butyl aluminum, triiso-butyl aluminum, trin-hexyl aluminum, trin-octyl aluminum, diethyl aluminum chloride, and ethyl aluminum dichloride.

17. The process according to claim 9, wherein the molar ratio of said 1,10-phenanthroline to $R_nAlX_m$ or Ph'$CH_2$Li ranges from 1:2.0 to 1:2.6.

* * * * *

UNITED STATES PATENT AND TRADEMARK OFFICE
CERTIFICATE OF CORRECTION

PATENT NO. : 9,266,982 B2
APPLICATION NO. : 13/991044
DATED : February 23, 2016
INVENTOR(S) : Jun Liu et al.

It is certified that error appears in the above-identified patent and that said Letters Patent is hereby corrected as shown below:

In The Claims

Claim 1, col. 35, line 63, "a $C_1$-$C_6$ alkly group" should read --a $C_1$-$C_6$ alkyl group--.

Claim 1, col. 35, line 66, "a $C_1$-$C_6$ alkly group" should read --a $C_1$-$C_6$ alkyl group--.

Claim 1, col. 36, lines 3-5, "$R_1$-$R_5$ being independently selected from a $C_1$-$C_6$ alkenyl or alkynyl group" should read --$R_1$-$R_5$ being independently selected from a $C_1$-$C_6$ alkyl group, a $C_2$-$C_6$ alkenyl or alkynyl group--.

Claim 7, col. 37, line 51, "$R_nAlX_m$" should read --$R_nAlX_m$--.

Claim 7, col. 38, line 1, "$R_nAlX_m$" should read --$R_nAlX_m$--.

Claim 9, col. 38, line 8, "$R_nAlX_m$" should read --$R_nAlX_m$--.

Claim 9, col. 38, line 10, "$R_nAlX_m$" should read --$R_nAlX_m$--.

Claim 10, col. 38, line 14, "$R_nAlX_m$" should read --$R_nAlX_m$--.

Claim 16, col. 38, line 51, "the halogenated alkylaluminuni $R_nAlX_m$" should read --the halogenated alkylaluminum $R_nAlX_m$--.

Signed and Sealed this
Fourteenth Day of June, 2016

Michelle K. Lee
*Director of the United States Patent and Trademark Office*